(12) United States Patent
Garneau-Tsodikova et al.

(10) Patent No.: US 10,173,968 B2
(45) Date of Patent: Jan. 8, 2019

(54) BISHYDRAZONE-BASED ANTIFUNGAL AGENTS

(71) Applicant: University of Kentucky Research Foundation, Lexington, KY (US)

(72) Inventors: Sylvie Garneau-Tsodikova, Lexington, KY (US); David S. Watt, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 15/644,677

(22) Filed: Jul. 7, 2017

(65) Prior Publication Data
US 2018/0009741 A1  Jan. 11, 2018

Related U.S. Application Data

(60) Provisional application No. 62/359,487, filed on Jul. 7, 2016.

(51) Int. Cl.
| | |
|---|---|
| *C07C 251/86* | (2006.01) |
| *C07D 279/22* | (2006.01) |
| *C07C 281/18* | (2006.01) |
| *C07C 251/82* | (2006.01) |

(52) U.S. Cl.
CPC .......... *C07C 251/86* (2013.01); *C07C 251/82* (2013.01); *C07C 281/18* (2013.01); *C07D 279/22* (2013.01); *C07C 2603/18* (2017.05)

(58) Field of Classification Search
CPC .................................................. C07C 251/86
USPC .......................................................... 544/35
See application file for complete search history.

(56) References Cited

FOREIGN PATENT DOCUMENTS

| GB | 76089 | * | 2/1957 |
| JP | 11080111 | * | 3/1999 |

OTHER PUBLICATIONS

Ehmer et al., Arzneimittel-Forschung, (1964) vol. 14(12), pp. 1273-1277.*
Volynskaya et al., Zhurnal Obshchei Khimi, (1973) vol. 43(5), pp. 1053-1057.*
Volynskaya et al., Zhurnal Obshchei Khimi, (1972) vol. 42(5), pp. 986-992.*
Kanakalakanmi et al., J. India Chem. Soc. (1969) vol. 46(5), pp. 444-450.*
Ngo, H. X.; Shrestha, S. K.; Garneau-Tsodikova, S. Identification of ebsulfur analogues with broad spectrum antifungal activity. ChemMedChem 2016, 11, 1507-1516.
Ngo, et al. Development of ebsulfur analogues as potent antibacterials against methicillin-resistant *Staphylococcus aureus*, Bioorganic & Medicinal Chemistry 24 (2016) 6298-6306.
Ngo et al. Supporting Information Identification of Ebsulfur Analogues with Broad-Spectrum Antifungal Activity; ChemMedChem 2016; pp. 1-7.
Ngo, et al. Supporting Information Development of ebsulfur analogues as potent antibacterials against methicillin-resistant *Staphylococcus aureus*, Bioorganic & Medicinal Chemistry (2016); pp. 1-53.

* cited by examiner

*Primary Examiner* — Taofiq A Solola
(74) *Attorney, Agent, or Firm* — Stites & Harbison PLLC; Mandy Wilson Decker

(57) ABSTRACT

Hydrazone compounds and pharmaceutical compositions including same are disclosed as having antifungal activity. Such compounds are useful for treating or preventing fungal conditions in a subject in need thereof by administering same.

8 Claims, 7 Drawing Sheets

BISHYDRAZONE-BASED ANTIFUNGAL AGENTS

RELATED APPLICATIONS

This application claims the benefit of U.S. Provisional Application Ser. No. 62/359,487, filed Jul. 7, 2016, the entire disclosure of which is incorporated herein by this reference.

GOVERNMENT INTEREST

This invention was made with government support by NIH grant AI090048 and NIH grants U01 DA013519, UL1TR000117 and T32 DA016176; and NIH grants P20 RR020171, CA172379 and CA187273. The Government has certain rights in the invention.

TECHNICAL FIELD

The present disclosure is directed to hydrazone compounds and pharmaceutical compositions including same having antifungal activity and methods for treating or preventing fungal conditions in a subject in need thereof by administering same.

BACKGROUND

The emergence of multidrug-resistant bacteria and fungi as human pathogens warrants a continued focus on the development of new pharmacophores for the treatment of these devastating and often fatal infections. The rise of multidrug-resistant bacteria, such as methicillin-resistant *Staphylococcus aureus* (MRSA) and vancomycin-resistant *Enterococci* (VRE), adversely affects the efficacy of many known, standard-of-care, antibacterial agents. Evidence of the impact of these multidrug-resistant strains appears in a 2011 report from the Centers for Disease Control and Prevention (CDC) that estimates that the national incidence of invasive MRSA infections was 80,461 cases and 650 deaths. This mortality rate is among the highest recorded for bacterial infections. Likewise, listerosis, which is a common foodborne illness caused by *Listeria monocytogenes*, represents a serious illness afflicting elderly people, newborns, and those with impaired immune systems. Estimates suggest that *L. monocytogenes* causes 19% of deaths associated with the consumption of contaminated foods in the United States.

The incidence of invasive fungal infections is also on the rise due to an increasing population of critically ill patients as a result of the human immunodeficiency virus (HIV), systemic diseases such as cancer, and the increasing role of organ transplantation. The National Healthcare Safety Network (NHSN) at the CDC has reported that *Candida* spp. ranked fifth among hospital-acquired pathogens. *Candida* spp. fungi have also been reported as the fourth most common causative pathogens of nosocomial, often fatal bloodstream infections. Eukaryotic *C. albicans* share a close evolutionary relationship as well as many cellular mechanisms with their human hosts and present therapeutic challenges for new treatments for systemic fungal infections. There is an unquestioned need for new antimicrobials that selectively inhibit these microorganisms without causing host toxicity.

Pentamidine represents an archetypical, biscationic antibiotic with a symmetrical structure containing two amidinium functional groups separated by a flexible 1,5-diphenoxypentane spacer. Developed initially as an antiprotozoal agent, it currently finds applications in both the treatment of protozoan diseases, such as *Trypanosoma brucei gambiense* (West African trypanosomiasis) as well as systemic fungal infections caused by *Pneumocystis jirovecii*, often seen in patients with HIV. Related compounds include symmetrical bisamidines, (e.g., furimidazoline), developed principally as topoisomerase inhibitors for cancer treatments. In addition to these biscationic compounds, other hydrazone- and guanidine-containing molecules possess a range of promising biological activities including antituberculosis, anti-HIV, anticonvulsant, anticancer, anti-inflammatory, antimalarial, antibacterial, and antifungal activities. Recently, bis(N-amidino)hydrazones were reported to inhibit the calcium-dependent serine endoprotease, furin, which activates immature proteins to their functional, mature form.

Accordingly, a continuing need exists for the development of specific antifungal agents for the treatment and prevention of fungal diseases and infections.

SUMMARY

The presently-disclosed subject matter meets the above-identified needs, as will become evident to those of ordinary skill in the art after a study of information provided in this document. Advantages of the present disclosure include antifungal agents and pharmaceutical compositions including same for the treatment or prevention of a fungal condition in a subject in need thereof.

This summary describes several embodiments of the presently-disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this summary or not. To avoid excessive repetition, this summary does not list or suggest all possible combinations of such features.

Provided herein, in some embodiments, is an antifungal composition comprising a compound according to formula (I):

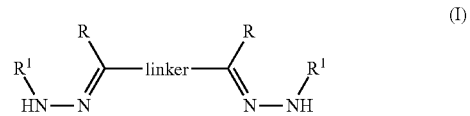

or a pharmaceutically acceptable salt thereof, wherein each R is independently H or a lower alkyl, wherein each $R^1$ is independently an amidino or an aryl, and wherein the linker comprises at least one aryl. In some embodiments, the linker comprises a polycyclic aryl according to formula (II):

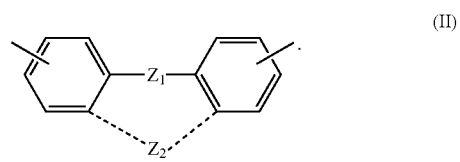

wherein $Z_1$ is selected from the group consisting of a single bond between the phenyl groups, a lower alkyl linking the phenyl groups, a $R^3$—Y—$R^3$ group, a chalcogen, and combinations thereof; wherein $Z_2$ is selected from the group consisting of not present, a lower alkyl, a $R^3$—Y—$R^3$ group, —C($R^4$)—, —C($R^4$)$_2$—, —N($R^5$)—, or a combination thereof; wherein each $R^3$ is independently a lower alkyl; wherein each $R^4$ is independently H or a lower alkyl; wherein $R^5$ is H or a lower alkyl; and wherein Y is a chalcogen. In some embodiments, the compound is a pharmaceutically acceptable hydrochloride salt.

In one embodiment, the compound is according to formula (III):

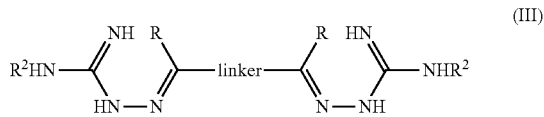

or a pharmaceutically acceptable salt thereof; wherein each $R^2$ is independently selected from the group consisting of H, a lower alkyl, an aryl, a substituted lower alkyl, a substituted aryl, and combinations thereof. The compounds having formula (III) are referred to herein as bis(N-amidino)hydrazones.

In another embodiment, the compound is according to formula (IV):

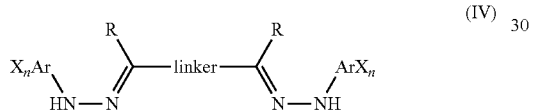

or a pharmaceutically acceptable salt thereof; wherein Ar is an aryl group; wherein each X is selected from the group consisting of electron-withdrawing groups such as, but not limited to, a halogen, a carbonyl group (e.g., —C(═O)R, —C(═O)OR, —C(═O)NR$_2$, or —CH(═O)), sulfoxide, sulfone, sulfonate, sulfonamide, a nitro group, a cyano group, or a combination thereof; and wherein each n is independently between 0 and 5, with 0 representing an unsubstituted aryl group. In some embodiments, each X is independently selected from the group consisting of fluorine, chlorine, and bromine. The compounds having formula (IV) are referred to herein as bis(N-aryl)hydrazones.

In another embodiment, the compound is according to formula (V):

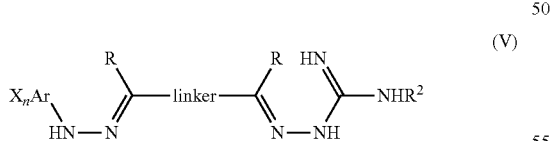

or a pharmaceutically acceptable salt thereof; wherein Ar is an aryl group; wherein each X is independently selected from the group consisting of electron-withdrawing groups such as, but not limited to, a halogen, a carbonyl group (e.g., —C(═O)R, —C(═O)OR, —C(═O)NR$_2$, or —CH(═O)), sulfoxide, sulfone, sulfonate, sulfonamide, a nitro group, a cyano group, or a combination thereof; wherein n is between 0 and 5, with 0 representing an unsubstituted aryl group; and wherein $R^2$ is selected from the group consisting of H, a lower alkyl, an aryl, a substituted lower alkyl, a substituted aryl, and combinations thereof. In some embodiments, each X is independently selected from the group consisting of fluorine, chlorine, and bromine. The compounds having formula (V) are referred to herein as N-amidino-N'-aryl-bishydrazones.

Also provided herein, in some embodiments, is a method for treating a fungal condition, the method comprising administering to a subject in need thereof a therapeutically effective amount of a compound according to formula (I):

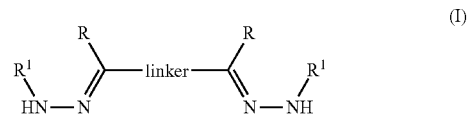

or a pharmaceutically acceptable salt thereof, wherein each R is independently H or a lower alkyl, wherein each $R^1$ is independently an amidino or an aryl, and wherein the linker comprises at least one aryl. In some embodiments, the linker comprises a polycyclic aryl according to formula (II):

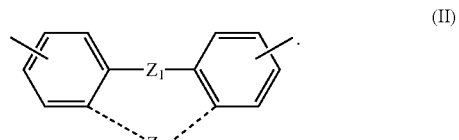

wherein $Z_1$ is selected from the group consisting of a single bond between the phenyl groups, a lower alkyl linking the phenyl groups, a $R^3$—Y—$R^3$ group, a chalcogen, and combinations thereof; wherein $Z_2$ is selected from the group consisting of not present, a lower alkyl, a $R^3$—Y—$R^3$ group, —C($R^4$)—, —C($R^4$)$_2$—, —N($R^5$)—, or a combination thereof wherein each $R^3$ is independently a lower alkyl; wherein each $R^4$ is independently H or a lower alkyl; wherein $R^5$ is H or a lower alkyl; and wherein Y is a chalcogen. In some embodiments, the compound is a pharmaceutically acceptable hydrochloride salt.

In one embodiment, the compound is according to formula (III):

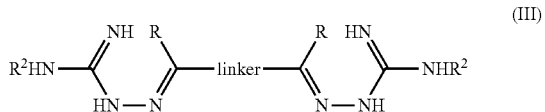

or a pharmaceutically acceptable salt thereof; wherein each $R^2$ is independently selected from the group consisting of H, a lower alkyl, an aryl, a substituted lower alkyl, a substituted aryl, and combinations thereof.

In another embodiment, the compound is according to formula (IV):

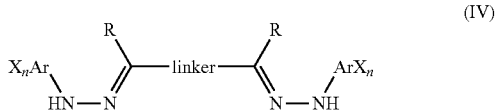

or a pharmaceutically acceptable salt thereof; wherein Ar is an aryl group; wherein each X is selected from the group consisting of electron-withdrawing groups such as, but not limited to, a halogen, a carbonyl group (e.g., —C(=O)R, —C(=O)OR, —C(=O)NR$_2$, or —CH(=O)), sulfoxide, sulfone, sulfonate, sulfonamide, a nitro group, a cyano group, or a combination thereof; and wherein each n is independently between 0 and 5, with 0 representing an unsubstituted aryl group. In some embodiments, each X is independently selected from the group consisting of fluorine, chlorine, and bromine.

In another embodiment, the compound is according to formula (IV):

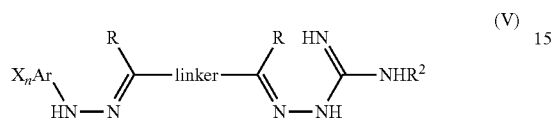

(V)

or a pharmaceutically acceptable salt thereof; wherein Ar is an aryl group; wherein each X is independently selected from the group consisting of electron-withdrawing groups such as, but not limited to, a halogen, a carbonyl group (e.g., —C(=O)R, —C(=O)OR, —C(=O)NR$_2$, or —CH(=O)), sulfoxide, sulfone, sulfonate, sulfonamide, a nitro group, a cyano group, or a combination thereof; wherein n is between 0 and 5, with 0 representing an unsubstituted aryl group; and wherein R$^2$ is selected from the group consisting of H, a lower alkyl, an aryl, a substituted lower alkyl, a substituted aryl, and combinations thereof. In some embodiments, each X is independently selected from the group consisting of fluorine, chlorine, and bromine.

Additional advantages of the present invention will become readily apparent to those skilled in this art from the following detailed description, wherein only the preferred embodiment of the invention is shown and described, simply by way of illustration of the best mode contemplated of carrying out the invention. As will be realized, the invention is capable of other and different embodiments, and its several details are capable of modifications in various obvious respects, all without departing from the invention. Accordingly, the drawings and description are to be regarded as illustrative in nature, and not as restrictive.

DETAILED DESCRIPTION OF THE DISCLOSURE

Figure 1A:
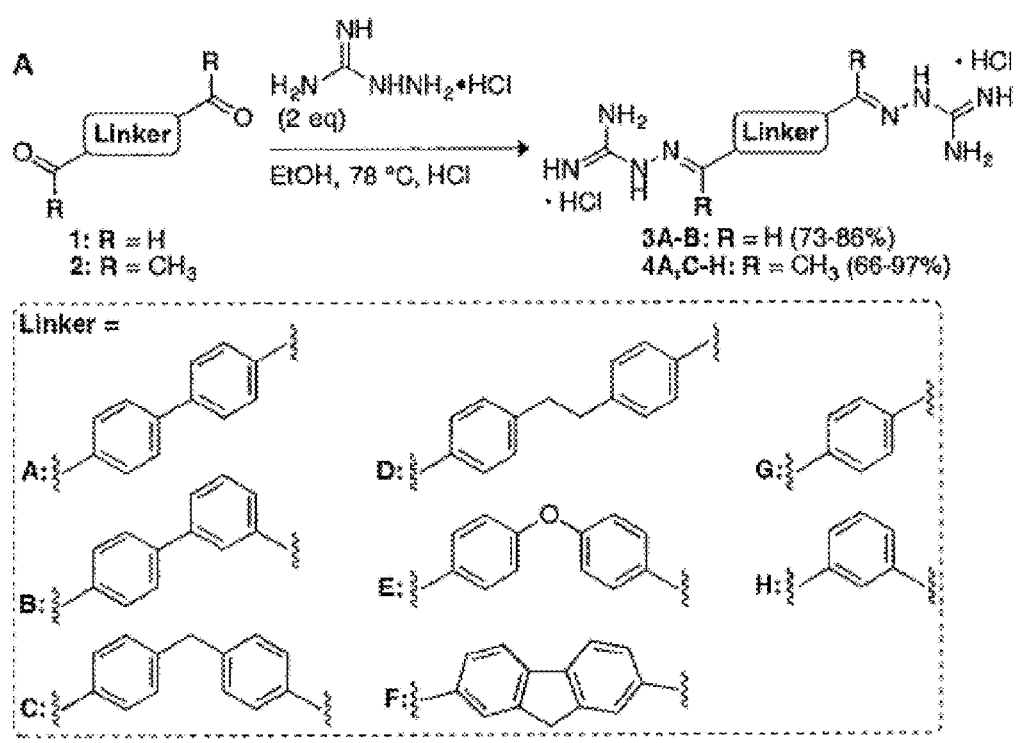
FIGS. 1A-B show schematic views of processes for synthesizing compounds of the present disclosure. (A) is a synthetic scheme for the preparation of bis(N-amidino) hydrazones according to embodiments of the present disclosure. (B) is a synthetic scheme for the preparation of bis(N-aryl)hydrazones and N-amidino-N'-aryl-bishydrazones according to embodiments of the present disclosure.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belong.

All patents, patent applications, published applications and publications, GenBank sequences, databases, websites and other published materials referred to throughout the entire disclosure herein, unless noted otherwise, are incorporated by reference in their entirety.

Where reference is made to a URL or other such identifier or address, it understood that such identifiers can change and particular information on the internet can come and go, but equivalent information can be found by searching the internet. Reference thereto evidences the availability and public dissemination of such information.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9): 1726-1732).

Although any methods, devices, and materials similar or equivalent to those described herein can be used in the practice or testing of the presently-disclosed subject matter, representative methods, devices, and materials are described herein.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the term "aryl" or "aryl group" refers to a substituent derived from an aromatic ring, including, but not limited to, a phenyl group, pyridyl and other heterocyclic variants, and/or naphthyl and other polycyclic variants. The term "substituted aryl" or "substituted aryl group," as used herein, refers to an aryl group where one or more hydrogen atoms has been replaced by an electron-withdrawing group. Unless stated otherwise, use of the term "aryl" or "aryl group" is intended to include "substituted aryl" or "substituted aryl group" throughout the instant disclosure.

The term "treat" and "treatment" refer to both therapeutic treatment and prophylactic or preventative measures, wherein the object is to prevent or slow down (lessen) an undesired pathological change or disorder, such as the development or spread of fungi. For purpose of this disclosure, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The presently-disclosed subject matter includes antifungal compounds having antifungal activity and pharmaceutical compositions including such compounds together with a pharmaceutically acceptable carrier. The antifungal compounds of the present disclosure are useful as antifungal agents and can inhibit the growth and reproduction of fungal cells and/or decrease the number of fungi. Accordingly, the antifungal compounds of the present disclosure can be used to treat or prevent a fungal condition, e.g., a fungal disease or infection, in a subject in need thereof. Subject as used herein refer to mammals and in particular to humans and domestic animals.

The antifungal compound of the instant disclosure includes a bishydrazone of the general formula (I):

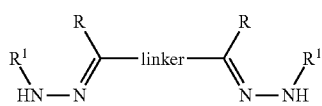
(I)

or a pharmaceutically acceptable salt thereof. For formula (I), each R is independently H or a lower alkyl, e.g., a $C_{1-6}$ alkyl such as a methyl or ethyl group. In one embodiment, each $R^1$ is independently an amidino (—C(=NH)NH$_2$) or an aryl group. In another embodiment, at least one $R^1$ is independently substituted with one or more electron-withdrawing groups such as, but not limited to, one or more halogens, one or more carbonyl groups (e.g., —C(=O)R, —C(=O)OR, —C(=O)NR$_2$, or —CH(=O)), one or more sulfoxide, one or more sulfone, one or more sulfonate, one or more sulfonamide, one or more nitro groups, one or more cyano groups, or a combination thereof.

The linker group of formula (I) includes any suitable moiety having at least one aryl group. For example, in one embodiment, the linker group includes a single aryl, radical, substituted aryl, or aryl derivative. Suitable single aryl linker groups include, but are not limited to:

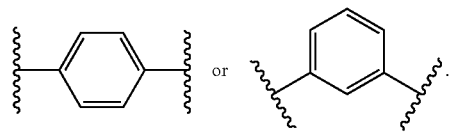

In another embodiment, the linker group is a polycyclic aryl according to formula (II):

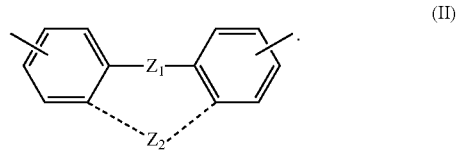
(II)

where $Z_2$ is optionally present in the linker group. $Z_1$ is a single bond between the phenyl groups, a lower alkyl linking the phenyl groups (e.g., a $C_{1-6}$ alkyl), a $R^3$—Y—$R^3$ group, a chalcogen (e.g., S; O), or a combination thereof. $Z_2$, when present, is a lower alkyl (e.g., a $C_{1-6}$ alkyl), $R^3$—Y—$R^3$ group, —C($R^4$)—, —C($R^4$)$_2$—, —N($R^5$)—, or a combination thereof. Each $R^3$ is independently a lower alkyl (e.g., a $C_{1-6}$ alkyl). Each $R^4$ is independently H or a lower alkyl (e.g., a $C_{1-6}$ alkyl). $R^5$ is H or a lower alkyl (e.g., a $C_{1-6}$ alkyl). Y is a chalcogen, e.g., O, S. Suitable linker groups according to formula (II) include, but are not limited to:

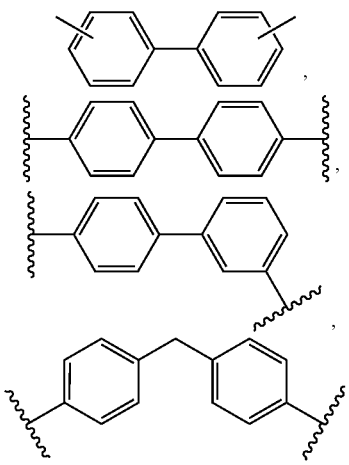

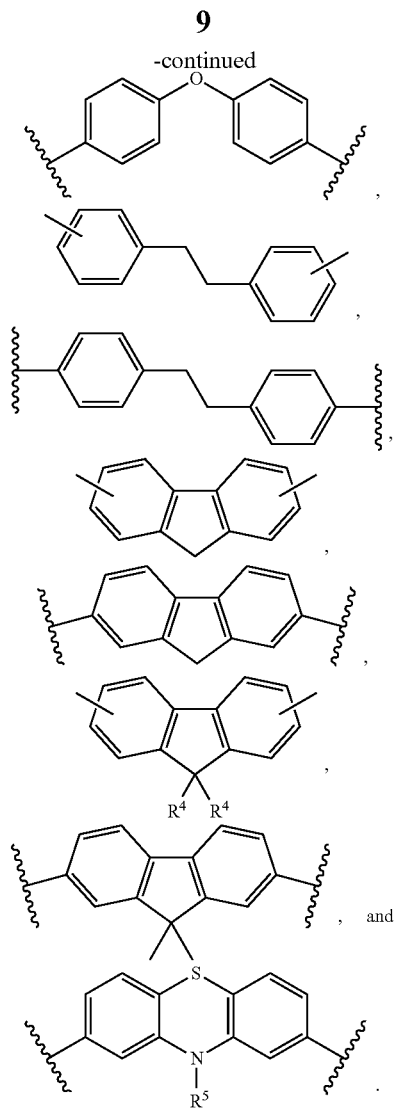

As will be understood by those skilled in the art, suitable linker groups are not limited to the specific examples above and may include any other structure or conformation encompassed by formula (II).

In some embodiments, each $R^1$ in the hydrazone of formula (I) is an amidino or substituted amidino group, according to formula (III):

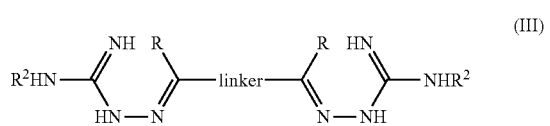

(III)

or a pharmaceutically acceptable salt thereof. For formula (III), each R is selected as described above with respect to formula (I). Additionally, each $R^2$ is independently H; a lower alkyl; an aryl; a substituted lower alkyl including, but not limited to, —$CH_2X$, $CH_2CH_2X$, or —$CH_2CH_2CH_2X$, where X includes fluorine, alkoxy (OR), or amino (e.g., NHR or $NR_2$); a substituted aryl; or a combination thereof. Suitable compounds according to formula (III) include, but are not limited to:

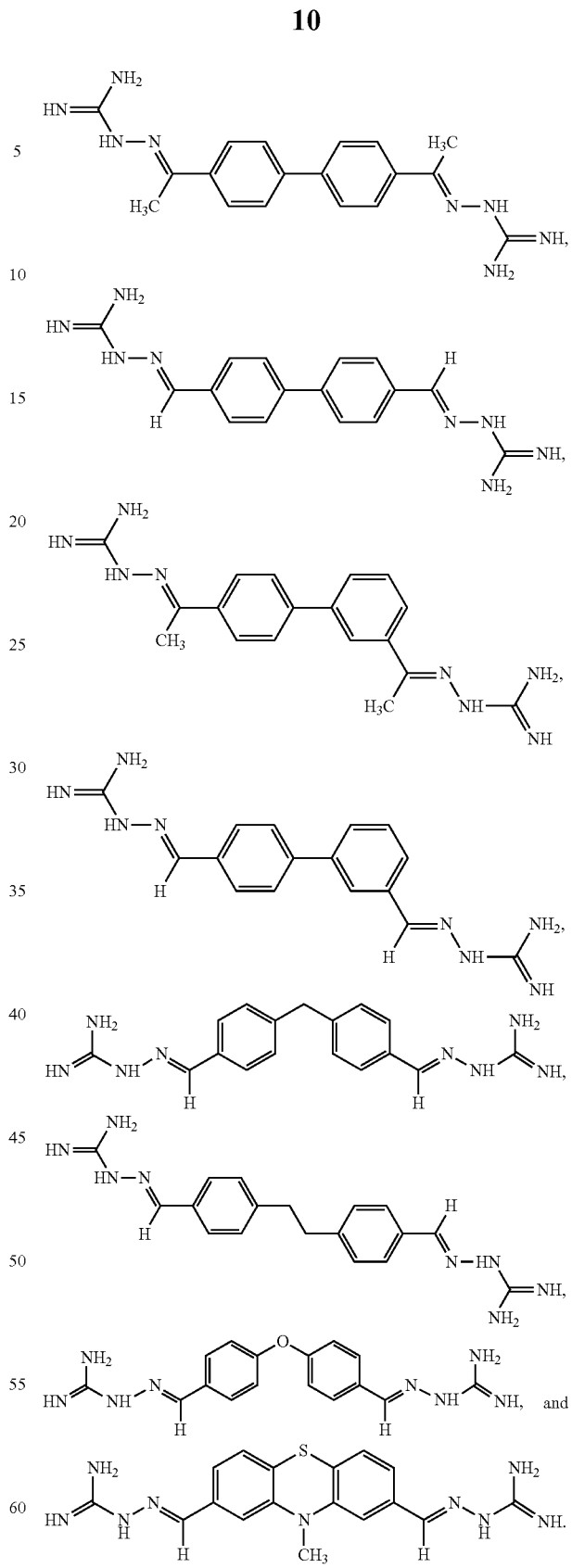

In other embodiments, each $R^1$ in the bishydrazone of formula (I) is an aryl or substituted aryl, according to formula (IV):

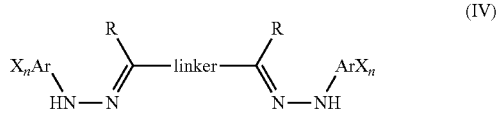

(IV)

or a pharmaceutically acceptable salt thereof. For formula (IV), each R is selected as described above with respect to formula (I). Ar is an aryl group (e.g., a phenyl group or a substituted phenyl group); X is an electron-withdrawing group such as, but not limited to, a halogen (e.g., fluorine, chlorine, bromine, iodine), a carbonyl group (e.g., —C(=O) R, —C(=O)OR, —C(=O)NR$_2$, or —CH(=O)), sulfoxide, sulfone, sulfonate, sulfonamide, a nitro group, a cyano group, or a combination thereof; and n represents the number of such electron-withdrawing groups on the aryl group, which can be 0 to 5, with 0 representing an unsubstituted aryl group. In one embodiment, for example, at least one of the aryl groups is substituted with one or more fluoro or one or more chloro groups, or both e.g., a fluorinated, chlorinated, difluorinated, dichlorinated, or fluoro-chloro substituted aryl group such as a halogenated phenyl group. Suitable compounds according to formula (IV) include, but are not limited to:

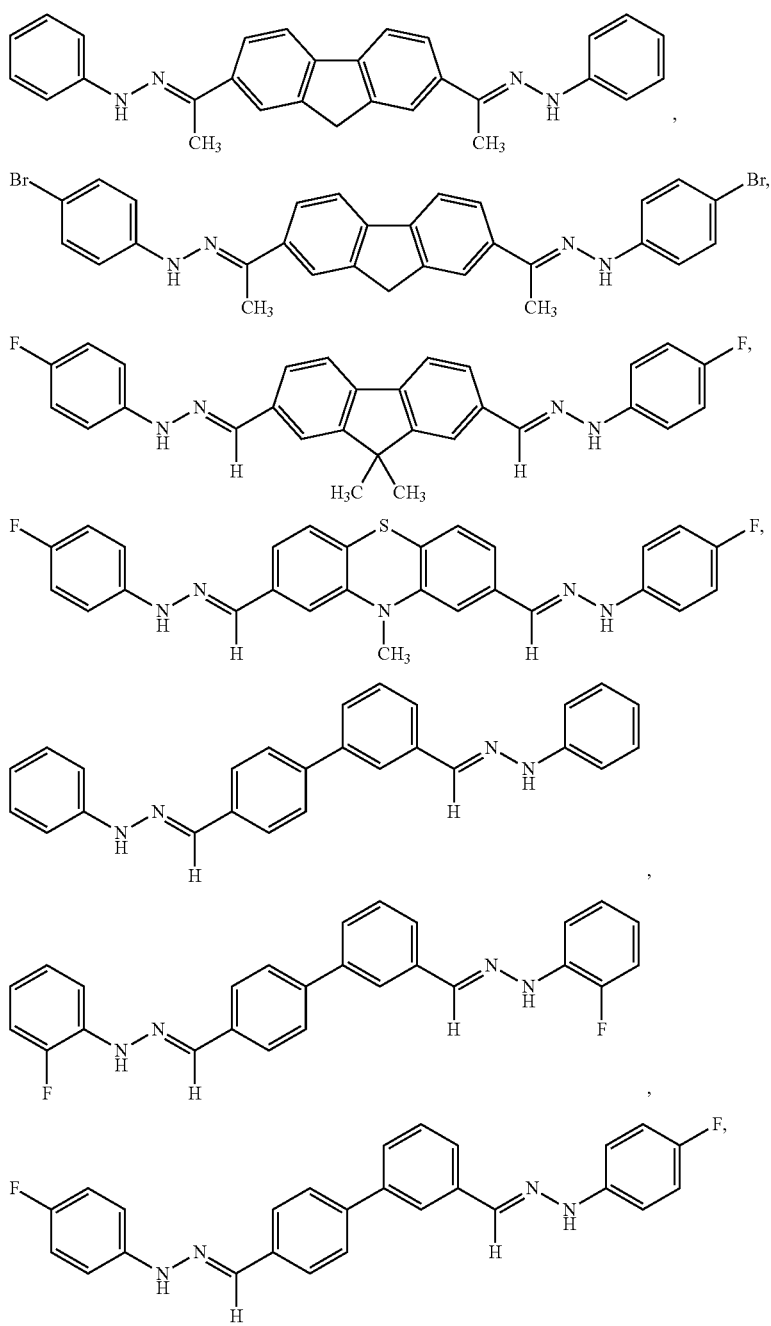

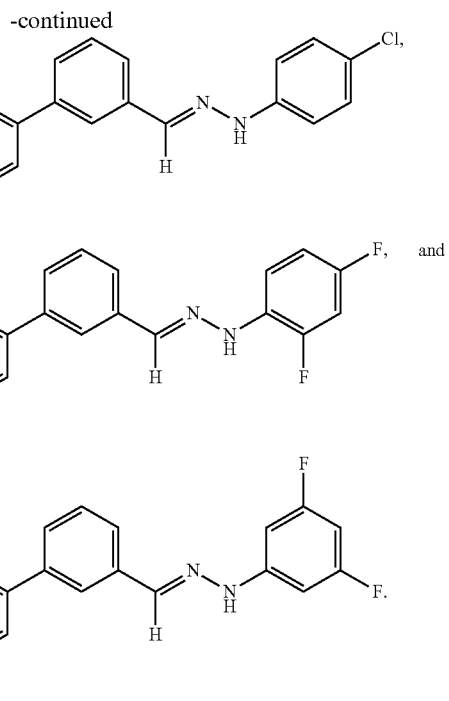

Alternatively, in some embodiments, one $R^1$ in the hydrazone of formula (I) is an amidino or substitute amidino, and the other $R^1$ is an aryl or substituted aryl, according to formula (V):

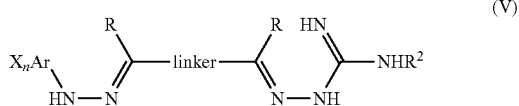

or a pharmaceutically acceptable salt thereof. For formula (V), each R is selected as described above with respect to formula (I). Ar is an aryl group (e.g., a phenyl group); X is an electron-withdrawing group such as, but not limited to, a halogen (e.g., fluorine, chlorine, bromine, iodine), a carbonyl group (e.g., —C(=O)R, —C(=O)OR, —C(=O)NR$_2$, or —CH(=O)), sulfoxide, sulfone, sulfonate, sulfonamide, a nitro group, cyano group, or a combination thereof; and n represents the number of such electron-withdrawing groups on the aryl group, which can be 0 to 5, with 0 representing an unsubstituted aryl group. $R^2$ is H; a lower alkyl; an aryl; a substituted lower alkyl including, but not limited to, —CH$_2$X, CH$_2$CH$_2$X, or —CH$_2$CH$_2$CH$_2$X, where X includes fluorine, alkoxy (OR), or amino (e.g., NHR or NR$_2$); a substituted aryl; or a combination thereof.

The compounds of formula (I) including a linker group according to one or more of the embodiments disclosed herein provide increased antibacterial and/or antifungal activities as compared to existing compounds. For example, in one embodiment, biscationic pharmacophores, such as the bis(N-amidino)hydrazones, bis(N-aryl)hydrazones, or N-amidino-N'-aryl-bishydrazones disclosed herein, with either a flexible or a rigid spacer, provide increased antibacterial and antifungal activities as compared to existing flexible bisamidines, as well as existing hydrazone- and guanidine-containing molecules currently found in the literature. Additionally, in some embodiments, the compounds disclosed herein provide antimicrobial activity without or substantially without developing drug resistance. Furthermore, in some embodiments, the compounds disclosed herein increase reactive oxygen species (ROS) production.

Accordingly, in some embodiments, the present disclosure includes methods for treating a fungal condition, e.g., a fungal disease, or fungal infection, by administering to a subject in need thereof a therapeutically effective amount of a compound according to formula (I), a pharmaceutically acceptable salt thereof, or a pharmaceutically acceptable composition including a compound according to formula (I) or a pharmaceutically acceptable salt thereof together with a pharmaceutically acceptable carrier. For example, in one embodiment, the method for treating a fungal condition includes administering to a subject in need thereof a therapeutically effective amount of a compound according to any one or more of formulae (III)-(V), pharmaceutically acceptable salts thereof, or a pharmaceutically acceptable composition including one or more compounds according to formulae (III)-(V) or pharmaceutically acceptable salts thereof together with a pharmaceutically acceptable carrier.

The phrase "therapeutically effective amount" means an amount of a compound of the present disclosure that (1) treats or prevents the particular disease, condition, or disorder, (2) attenuates, ameliorates, or eliminates one or more symptoms of the particular disease, condition, or disorder, or (3) prevents or delays the onset of one or more symptoms of the particular disease, condition, or disorder described herein. In the case of fungal infection, the therapeutically effective amount of the drug may be to inhibit the growth and/or reproduction of fungal cells and/or decrease the number of fungi and/or relieve to some extent one or more of the symptoms associated with a fungal condition such as a fungal disease or infection in a subject.

EXAMPLES

The following examples are intended to illustrate certain preferred embodiments of the invention and are not limiting in nature. Those skilled in the art will recognize, or be able to ascertain, using no more than routine experimentation, numerous equivalents to the specific substances and procedures described herein.

Example 1

To show the potential of various compounds disclosed herein, nine symmetrical bis(N-amidino)hydrazones (3A-B and 4A,C-H) and eight asymmetrical N-amidino-N'-aryl-bishydrazones (7Aa-Ag and 8Aa) (Scheme 1, FIGS. A-B) were synthesized, and their antibacterial and antifungal activities were evaluated against panels of bacterial strains (four Gram-positive, six Gram-negative, and one mycobacterial) and seven *Candida albicans* strains. Because the development of resistance represents a crucial problem in antimicrobial drug development, the potential of resistance development by bacteria and fungi against these compounds was also established. Additionally, the production of reactive oxygen species (ROS) was measured in yeast cells of some of these compounds, and the compounds in vitro cytotoxicity as well as the compounds minimal affinity, which is desired, for the hERG potassium channel was determined. The combination of testing new antimicrobial agents and early screening for resistance and toxicity represent an avenue most likely to produce pharmacophores of potential utility in disease treatment.

Figure 1B:
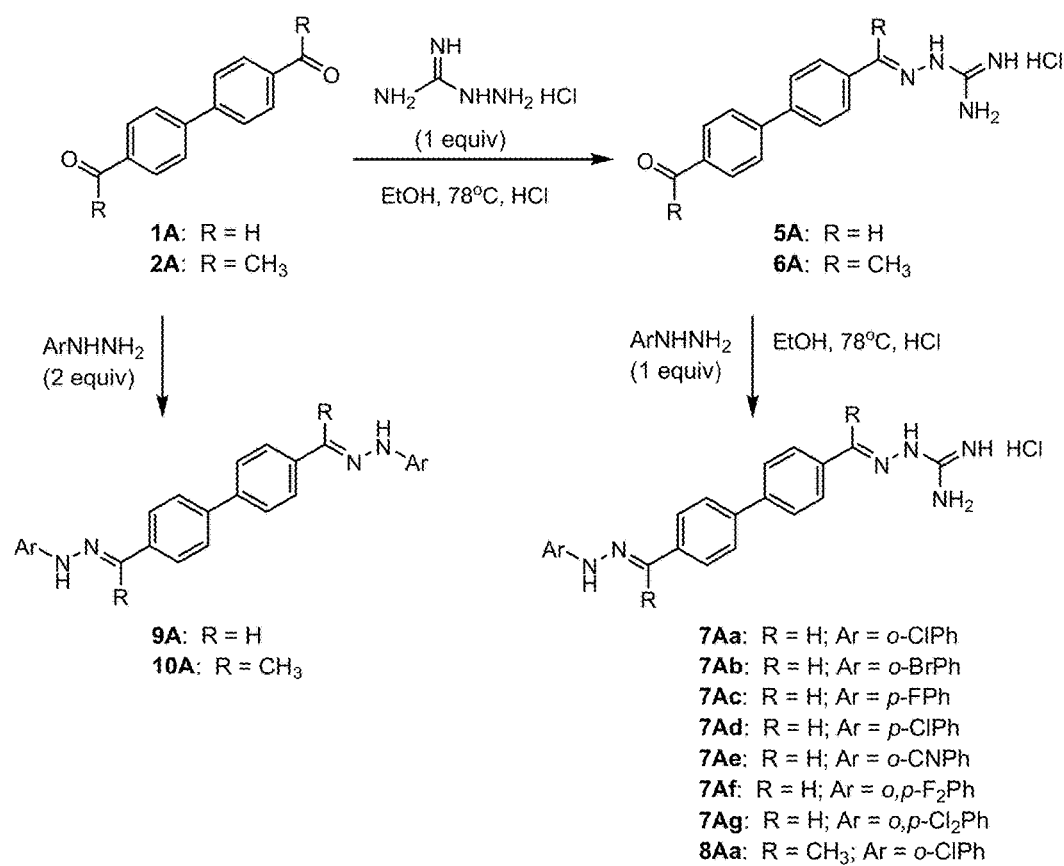

Chemical Synthesis of Biscationic Compounds with Two, Chemically Identical Termini To form the biscationic hydrazones of formula (III) with two N-amidino groups, the carbonyl groups in either bisaldehyde 1 or bisketone 2, which in some cases were in regiochemically distinct positions in the spacer (e.g., 1B, 2B, 2H), were modified with N-aminoguanidine hydrochloride to obtain the biscationic products 3 and 4, respectively (FIG. 1A). To form the biscationic hydrazones of formula (IV) with two N-aryl groups, the carbonyl groups in either bisaldehyde 1 or bisketone 2, which in some cases were in regiochemically distinct positions in the spacer (e.g., 1B, 2B, 2H), were modified with N-arylhydrazines to obtain the biscationic products 9 and 10, respectively (FIG. 1B).

Design and Chemical Synthesis of Biscationic Compounds with Chemically Non-Identical Termini Literature approaches for the synthesis of bicationic agents with two chemically non-identical termini typically involved the construction of the spacer as the ultimate step. For example, the coupling of an amidino-substituted naphthol with a guanidine-substituted benzoic acid secured biscationic esters with an amidinium group at one terminus and a guandinium group at the other. The synthetic approach that is reported here differed from this strategy in that a stepwise, chemoselective modification of bisaldehydes 1 or bisketones 2 was used to arrive at biscationic systems with different cationic groups at each terminus. Condensations of one equivalent of N-aminoguanidine hydrochloride with 1A and 2A led to the efficient production of monosubstituted N-amidinohydrazones 5A and 6A, respectively (FIG. 1B). The hydrochloride salts of these monocatioinic products were readily crystallized and thereby were isolated free from starting materials and suitable for the subsequent synthesis of the biscationic agents. For example, the subsequent treatment of 5A and 6A with N-arylhydrazines furnished the desired, biscationic agents 7Aa-Ag and 8Aa, respectively, which we describe as N-amidino-N'-aryl-bishydrazones (FIG. 1B). Cavallini described the monocationic N-amidinohydrazones as antibacterial agents some years ago, but the range of organisms and $MIC_{50}$ values were, in general, unimpressive. No effort was made by Cavallini to examine organisms which represent the most imminent threat to human health.

The antibacterial and antifungal properties of bis(N-amidino)hydrazones 3 and 4 and N-amidino-N'-aryl-bishydrazones 7 and 8 were evaluated as discussed below.

Antibacterial Activity

To determine if bis(N-amidino)hydrazones and N-amidino-N'-aryl-bishydrazones displayed antibacterial activity, compounds 3A-8Aa were evaluated against a panel of Gram-positive (4 strains), Gram-negative (6 strains), and one mycobacterial strain using the aminoglycoside amikacin (AMK), the β-lactam ampicillin (AMP), and the fluoroquinolone ofloxacin (OFX) as positive controls in a concentration range of 0.5-500 µM. The results are provided in Table 1 below.

TABLE 1

MIC values in µg/mL and (µM)[a] for compounds 3A, B, 4A, C-H, 7Aa-Ag, and 8Aa against various bacterial strains.

| | Gram-positive | | | | Gram-negative | |
|---|---|---|---|---|---|---|
| Cpd | A | B | C | D | E | F |
| AMK | 3.0-12.2 (3.9-15.6) | 3.0 (3.9) | 24.5 (31.3) | 97.7 (125) | 24.5 (31.3) | 48.9 (62.5) |
| AMP | >92.8 (>250) | 92.8 (250) | 92.8 (250) | 92.8 (250) | >92.8 (>250) | >92.8 (>250) |
| OFX | ≤0.2 (≤0.5) | 0.4 (1.0) | 0.4 (1.0) | 2.8 (7.8) | ≤0.2 (≤0.5) | ≤0.2 (≤0.5) |
| 3A | >198 (>500) | 0.4 (1.0) | 1.5 (3.9) | 0.8 (2.0) | >198 (>500) | >198 (>500) |
| 3B | >198 (>500) | 0.4 (1.0) | 1.5 (3.9) | 1.5 (3.9) | >198 (>500) | >198 (>500) |
| 4A | >212 (>500) | >212 (>500) | >212 (>500) | >212 (>500) | >212 (>500) | 52.9 (125) |
| 4C | >219 (>500) | 1.7 (3.9) | 1.7 (3.9) | 0.9 (2.0) | >219 (>500) | >219 (>500) |
| 4D | >226 (>500) | 0.5 (1.0) | 0.5-0.9 (1.0-2.0) | 0.5 (1.0) | >226 (>500) | >226 (>500) |
| 4E | 54.9 (125) | 27.5 (62.5) | 54.9 (125) | 1.7 (3.9) | 27.5 (62.5) | 110 (250) |
| 4F | 3.4 (7.8) | <0.2 (<0.5) | 0.4-0.9 (1.0-2.0) | 0.4 (1.0) | 218 (500) | 218 (500) |
| 4G | 86.8 (250) | 86.8 (250) | >173 (>500) | 43.4 (125) | 173 (500) | >173 (>500) |
| 4H | 86.8 (250) | 86.8 (250) | >173 (>500) | 43.4 (125) | >173 (>500) | >173 (>500) |
| 7Aa | >215 (>500) | 0.4-0.9 (1.0-2.0) | 0.9 (2.0) | 0.9 (2.0) | >215 (>500) | >215 (>500) |
| 7Ab | >235 (>500) | 0.9 (2.0) | 0.9 (2.0) | 0.9 (2.0) | >235 (>500) | >235 (>500) |

TABLE 1-continued

MIC values in μg/mL and (μM)$^a$ for compounds 3A, B, 4A, C-H, 7Aa-Ag, and 8Aa against various bacterial strains.

| | | | | | | |
|---|---|---|---|---|---|---|
| 7Ac | >205 (>500) | 0.8 (2.0) | 3.2 (7.8) | 1.6 (3.9) | >205 (>500) | >205 (>500) |
| 7Ad | >214 (>500) | 1.7 (3.9) | 3.3 (7.8) | 1.7 (3.9) | >214 (>500) | >214 (>500) |
| 7Ae | 13.1 (31.3) | 3.3 (7.8) | 6.5 (15.6) | 0.8-1.6 (2.0-3.9) | 6.5-13.1 (15.6-31.3) | 209 (500) |
| 7Af | >214 (>500) | 0.9-1.7 (2.0-3.9) | 1.7 (3.9) | 1.7 (3.9) | >214 (>500) | >214 (>500) |
| 7Ag | >231 (>500) | 3.6 (7.8) | 3.6 (7.8) | 3.6 (7.8) | >231 (>500) | >231 (>500) |
| 8Aa | 26.6-53.3 (62.5-125) | 26.6-53.3 (62.5-125) | 53.3 (125) | 1.7 (3.9) | 26.6 (62.5) | 213 (500) |

| | | Gram-negative | | | | |
|---|---|---|---|---|---|---|
| Cpd | G | H | I | J | K | |
| AMK | 24.5 (31.3) | 24.5 (31.3) | 48.9 (62.5) | 3.0-6.1 (3.9-7.8) | 12.2 (15.6) | |
| AMP | >92.8 (>250) | >92.8 (>250) | >92.8 (>250) | 92.8 (250) | >92.8 (>250) | |
| OFX | 1.4-2.8 (3.9-7.8) | 5.6-11.3 (15.6-31.3) | 1.4 (3.9) | 5.6-11.3 (15.6-31.3) | 5.6 (15.6) | |
| 3A | >198 (>500) | >198 (>500) | >198 (>500) | >198 (>500) | >198 (>500) | |
| 3B | >198 (>500) | >198 (>500) | >198 (>500) | >198 (>500) | 0.4 (1.0) | |
| 4A | 26.5 (62.5) | 6.6 (15.6) | 0.8 (2.0) | >212 (>500) | >212 (>500) | |
| 4C | >219 (>500) | >219 (>500) | >219 (>500) | >219 (>500) | 0.9 (2.0) | |
| 4D | >226 (>500) | >226 (>500) | >226 (>500) | >226 (>500) | 0.5 (1.0) | |
| 4E | 54.9 (125) | 27.5 (62.5) | 27.5 (62.5) | 54.9 (125) | 54.9-110 (125-250) | |
| 4F | 218 (500) | 13.6-27.2 (31.3-62.5) | 0.4-0.9 (1.0-2.0) | 1.7 (3.9) | 0.4 (1.0) | |
| 4G | >173 (>500) | 173 (500) | 86.8 (250) | 86.8-173 (250-500) | >173 (>500) | |
| 4H | >173 (>500) | >173 (>500) | 173 (500) | 21.7-86.8 (62.5-250) | 5.4 (15.6) | |
| 7Aa | >215 (>500) | >215 (>500) | >215 (>500) | >215 (>500) | 1.7 (3.9) | |
| 7Ab | >235 (>500) | >235 (>500) | >235 (>500) | >235 (>500) | 1.8 (3.9) | |
| 7Ac | >205 (>500) | >205 (>500) | >205 (>500) | >205 (>500) | 1.6 (3.9) | |
| 7Ad | >214 (>500) | >214 (>500) | >214 (>500) | >214 (>500) | 1.7 (3.9) | |
| 7Ae | 26.1-52.2 (62.5-125) | 6.5-13.1 (15.6-31.3) | 13.1-26.1 (31.3-62.5) | 6.5 (15.6) | 6.5-13.1 (15.6-31.3) | |
| 7Af | >214 (>500) | >214 (>500) | >214 (>500) | >214 (>500) | 0.9-1.7 (2.0-3.9) | |
| 7Ag | >231 (>500) | >231 (>500) | >231 (>500) | >231 (>500) | 1.8 (3.9) | |
| 8Aa | 213 (500) | 26.6-53.3 (62.5-125) | 213 (500) | 26.3-53.3 (62.5-125) | 213 (500) | |

$^a$These antibacterial MIC values were originally determined in μM using a range of 0.5 to 500 μM. These values are presented into parentheses. The values in μg/mL are presented for comparison with the antifungal MIC values which were originally determined in μg/mL.
Gram-positive: A = *B. subtilis* 168, B = *L. monocytogenes* ATCC 19115, C = MRSA, D = VRE.
Gram-negative: E = *A. baumannii* ATCC 19606, F = *E. cloacae* ATCC 13047, G = *E. coli* MC1061, H = *K. pneumoniae* ATCC 27736, I = *P. aeruginosa* ATCC 27853, J = *S. enterica* ATCC 14028.
Mycobacterial: K = *M. smegmatis* MC2-155.
Control antibiotics: AMK = amikacin, AMP = ampicillin, OFX = ofloxacin.

In general, the compounds displayed excellent (MIC values ≤0.5-7.8 μM), intermediate (15.6-31.3 μM), or low (62.5-≥500 μM) antibacterial activity against the bacterial strains tested.

Overall, when analyzing the MIC data obtained against the Gram-positive bacterial strains (strains A-D), it was noticed that most of the bis(N-amidino)hydrazones (3A,B, 4C,D, 4F) and N-amidino-N'-aryl-bishydrazones (7Aa-Ad, and 7Af-Ag) showed excellent antibacterial activity against *Listeria monocytogenes* ATCC 19115 (strain B) (MIC <0.5-7.8 μM), methicillin-resistant *Staphylococcus aureus* (MRSA) (strain C) (MIC=1.0-7.8 μM), and vancomycin-resistant enterococcus (VRE) (strain D) (MIC=1.0-7.8 μM). All of the compounds displayed poor activity against *Bacillus subtilis* 168 (strain A), with the exception of compound 4F, which displayed good activity (MIC=7.8 μM) against this strain. Likewise, compound 7Ae exhibited excellent antibacterial activity against *L. monocytogenes* ATCC 19115 (strain B; MIC=7.8 μM) and VRE (strain D; MIC=2.0-3.9 μM) but only moderate antibacterial activity against *B. subtilis* 168 (strain A; MIC=31.3 μM) and MRSA (strain C; MIC=15.6 μM), respectively. Overall, compound 4F was found to be the most active against Gram-positive bacteria.

Compound 4A exhibited potent activity against *P. aeruginosa* ATCC 27853 (strain I; MIC=2.0 μM) and moderate activity against *Klebsiella pneumoniae* ATCC 27736 (strain H; MIC=15.6 μM). Similarly, compound 4F also displayed excellent antibacterial activities against strain I (MIC=1.0-2.0 μM) and *S. enterica* ATCC 14028 (strain J; MIC=3.9 μM), as well as moderate to low activity against strain H (MIC=31.3-62.5 μM). Additionally, 7Ae showed only moderate antibacterial activities against strain H (MIC=15.6-31.3 μM), strain I (MIC=31.3-62.5 μM), and strain J (MIC=15.6 μM). Compounds 3B, 4C-D, 4F, 7Aa-Ad, and 7Af-Ag exhibited excellent antibacterial activity (MIC values ranging from 1.0-3.9 μM) against *M. smegmatis* MC2-155 (strain K), whereas compounds 4H and 7Ae showed only moderate activity (15.6-31.3 μM) and compounds 3A, 4A, 4E, 4G, and 8Aa showed low activity (125→500 μM) against this mycobacterial strain. It is noteworthy to mention that when compared to clinically relevant antibacterial drugs, such as AMK (MIC=3.9-125 μM), AMP (MIC≥250 μM), and OFX (MIC≤0.5-31.3 μM), the compounds reported here showed either superior or comparable antibacterial activity against all bacterial strains tested relative to these clinical agents.

Antifungal Activity

The antifungal activity of the bis(N-amidino)hydrazones and N-amidino-N-aryl-bishydrazones was determined against a panel of seven *Candida albicans* strains in a concentration range of 0.5-31.3 μg/mL. The results are provided in Table 2 below.

TABLE 2

MIC values in μg/mL[a] and (μM) for compounds 3A, B, 4A, C-H, 7Aa-Ag, and 8Aa against various *C. albicans* strains.

| Cpd | 1003[a] | 1237[b] | 2310[c] | 2876[c] | 10231[b] | 64124[b] | 90819[b] |
|---|---|---|---|---|---|---|---|
| AmB | 3.9 (4.2) | 3.9 (4.2) | 3.9 (4.2) | 3.9 (4.2) | 3.9 (4.2) | 2.0-3.9 (2.1-4.2) | 2.0 (2.1) |
| 3A | 7.8 (19.7) | 15.6 (39.5) | >31.3 (>79.2) | 7.8 (19.7) | 15.6 (39.5) | >31.3 (>79.2) | >31.3 (>79.2) |
| 3B | 3.9 (9.9) | 3.9 (9.9) | 3.9 (9.9) | 3.9 (9.9) | 3.9 (9.9) | 3.9 (9.9) | 3.9 (9.9) |
| 4A | 7.8 (18.4) | >31.3 (>73.9) | 3.9 (9.2) | 2.0 (4.7) | 2.0-3.9 (4.7-9.2) | 2.0 (4.7) | 3.9 (9.2) |
| 4C | 7.8 (17.8) | 7.8 (17.8) | 7.8 (17.8) | 3.9 (8.9) | 7.8 (17.8) | 7.8 (17.8) | 7.8 (17.8) |
| 4D | 15.6 (34.6) | 15.6 (34.6) | 31.3 (69.3) | 3.9 (8.6) | 7.8 (17.3) | >31.3 (>69.3) | 7.8 (17.3) |
| 4E | 7.8 (17.8) | 7.8 (17.8) | 7.8 (17.8) | 3.9 (8.9) | 7.8 (17.8) | 7.8 (17.8) | 7.8 (17.8) |
| 4F | 1.0 (2.3) | 2.0 (4.6) | 1.0 (2.3) | 1.0 (2.3) | 1.0-2.0 (2.3-4.6) | 1.0 (2.3) | 2.0 (4.6) |
| 4G | >31.3 (>90.1) | >31.3 (>90.1) | >31.3 (>90.1) | >31.3 (>90.1) | >31.3 (>90.1) | 31.3 (90.1) | >31.3 (>90.1) |
| 4H | >31.3 (>90.1) | 31.3 (90.1) | 31.3 (90.1) | 7.8 (22.5) | >31.3 (>90.1) | >31.3 (>90.1) | >31.3 (>90.1) |
| 7Aa | 2.0 (4.6) | 3.9 (9.2) | 2.0 (4.6) | 2.0 (4.6) | 2.0 (4.6) | 3.9 (9.2) | 2.0 (4.6) |
| 7Ab | 2.0 (4.1) | 3.9 (8.3) | 3.9 (8.3) | 3.9 (8.3) | 2.0 (4.1) | 3.9 (8.3) | 3.9 (8.3) |
| 7Ac | 2.0 (4.7) | 7.8 (19.0) | 3.9 (9.5) | 3.9 (9.5) | 7.8 (19.0) | 31.3 (76.2) | 3.9 (9.5) |
| 7Ad | 3.9 (9.1) | 15.6 (36.5) | 3.9 (9.1) | 7.8 (18.3) | 7.8 (18.3) | 15.6 (36.5) | 7.8 (18.3) |
| 7Ae | 7.8 (18.7) | 15.6 (37.3) | 15.6 (37.3) | 15.6 (37.3) | 15.6 (37.3) | 31.3 (74.9) | 15.6 (37.3) |
| 7Af | 2.0 (4.5) | 3.9 (9.1) | 3.9 (9.1) | 3.9 (9.1) | 1.0 (2.3) | 3.9 (9.1) | 7.8 (18.2) |
| 7Ag | 7.8 (16.8) | 15.6 (33.8) | 7.8 (16.8) | 15.6 (33.8) | 7.8 (16.8) | 31.3 (67.8) | 31.3 (67.8) |
| 8Aa | 15.6 (34.3) | 15.6 (34.3) | 15.6 (34.3) | 15.6 (34.3) | 15.6 (34.3) | 31.3 (68.7) | 15.6 (34.3) |

[a]These antifungal MIC values were originally determined in □g/mL using a range of 0.5 to 31.3 μg/mL. The values in μM into parentheses are presented for comparison with the antibacterial MIC values which were originally determined in μM.
[b]Indicates strains that are resistant to FLC, ITC, and VOR according to ATCC.
[c]Indicates strains that are susceptible to FLC, ITC, and VOR according to ATCC.
Control antifungal agent: AmB = amphotericin B.

The common antifungal agent amphotericin B (AmB) was used as a positive control. It was observed that compounds 3B, 4F, 7Aa, 7Ab, and 7Af showed excellent antifungal activities against all fungal strains tested, with 4F showing superior (MIC=1.0-3.9 μg/mL) activity. Similarly, compound 4A also displayed potent antifungal activities (MIC=2.0-3.9 μg/mL) against most strains except against *C. albicans* ATCC 1003 (MIC=7.8 μg/mL) and *C. albicans* ATCC 1237 (MIC=31.3 μg/mL). Compounds 7Ad, 7Ae, 7Ag, and 8Aa showed only moderate fungal growth inhibition (MIC=7.8-15.6 μg/mL) against the majority of the fungal strains with the exception of *C. albicans* ATCC 64124 (MIC=31.3 μg/mL for 7Ae, 7Ag, and 8Aa), *C. albicans* ATCC 90819 (MIC=31.3 μg/mL for 7Ag), *C. albicans* ATCC 1003 (MIC=3.9 μg/mL for 7Ad) and *C. albicans* ATCC 2310 (MIC=3.9 μg/mL for 7Ad). Compounds 7Ac also exhibited excellent growth inhibition against most of the fungal strains tested, except against *C. albicans* ATCC 10231 (moderate activity, MIC=7.8 μg/mL) and *C. albicans* ATCC 64124 (poor activity, MIC=31.3 μg/mL). It is important to emphasize that most of the bis(N-amidino)hydrazones and N-amidino-N-aryl-bishydrazones displayed either superior or comparable antifungal activities against the majority of the fungal strains tested, when compared to the clinically relevant antifungal agents, AmB (MIC=2.0-3.9 μg/mL).

SAR Analysis.

Variations in SAR outcomes for compounds studied as antibacterial or as antifungal agents was expected given that bacteria are prokaryotic organisms and fungi are eukaryotic organisms.

Based upon the antibacterial and antifungal results presented in Tables 1 and 2, it was determined that with respect to bis(N-amidino)hydrazones, linkers comprised of a single phenyl ring, regardless of its substitution pattern (para or meta, as in compounds 4G and 4H, respectively), displayed diminished but not non-existent antimicrobial activity as compared to the other linkers disclosed herein. Additionally, comparing the MIC value profiles of compounds 3A and 4A as well as 7Aa and 8Aa, which only differ by the absence or presence of a methyl group on the carbons alpha to the phenyl rings indicated that the methyl group diminished antibacterial activity of these compounds relative to cases where the carbons alpha to the phenyl rings contained a hydrogen. However, the presence of the methyl group appeared beneficial in terms of antifungal activity. For example, compound 4A was overall a much better antifungal agent than compound 3A. Turning to the antibacterial MIC values for compounds 3A and 3B, it was observed that they were about equivalent in all cases, except against strain K where the MIC value for compound 3B (MIC=1 μM) was much lower than that for compound 3A (MIC>500 μM). From these data, it was deduced that the substitution patterns of the biphenyl linkers had minimal effects on antibacterial activity. However, the substitution patterns of the biphenyl linkers were found to have a substantial effect on antifungal activity. For example, compound 3B was a much better antifungal agent than compound 3A.

With respect to the length of the flexible, linear, alkyl spacer between the two phenyl rings, comparing the MIC values of compounds 4A, 4C, and 4D, once again showed opposing trends in antibacterial and antifungal activities. In particular, increasing the length of the flexible alkyl linker between the two phenyl rings resulted in a decrease in antibacterial MIC values, whereas this same increase in the length of the linker resulted in an increase in antifungal MIC values. As to rigidity of the linker, by contrasting the MIC value profile of compound 4C containing a flexible linker to that of compound 4F containing a rigid linker, it was concluded that introducing rigidity in the linker was beneficial for antimicrobial activity. In contrast to rigidity, a comparison of the MIC value profiles of compounds 4C and 4E indicated that replacing the methylene bridging the two phenyl groups of the linker with an oxygen atom had no effect on antifungal activity, but was detrimental to antibacterial activity.

Next, by comparing compounds 7Aa-7Ag, it was observed that the nature of the substituent in the ortho position of the mono-substituted aryl group of compounds 7Aa and 7Ab did not affect antibacterial or antifungal activity, whereas the nature of the substituent in the para position of the mono-substituted aryl group of compounds 7Ac-7Ae had the opposing effects on antibacterial (CN>halogen) and antifungal (halogen>CN) activity. It was also observed that the o,p-difluorinated and o,p-dichlorinated aryl moieties of compounds 7Af and 7Ag had similar overall antibacterial activity, but different antifungal activity, in which the o,p-difluorinated group possessed improved antifungal activity. Finally, with regard to the effect of substitution pattern of the aryl ring (ortho versus para-monosubstituted versus ortho,para-disubstituted) on antimicrobial activity, a comparison of the activity resulting from different chlorination patterns in compounds 7Aa (ortho), 7Ad (para), and 7Ag (o,p-diCl), indicated that these changes had minimal effects on antibacterial activity but substantial effects on antifungal activity. The o-chlorinated N-amidino-N-aryl-bishydrazone was superior to the p-chlorinated analog, which in turn was much better than o,p-dichlorinated analog.

Development of Bacterial and Fungal Resistance Studies

The emergence of antibiotic resistance by microbes is an inevitable process; however, the frequency at which resistance develops varies from one antibiotic to another. It is critical to assess the ability of new antimicrobials to evade, as long as possible, the development of bacterial and fungal resistance early in the development process.

Figure 2:
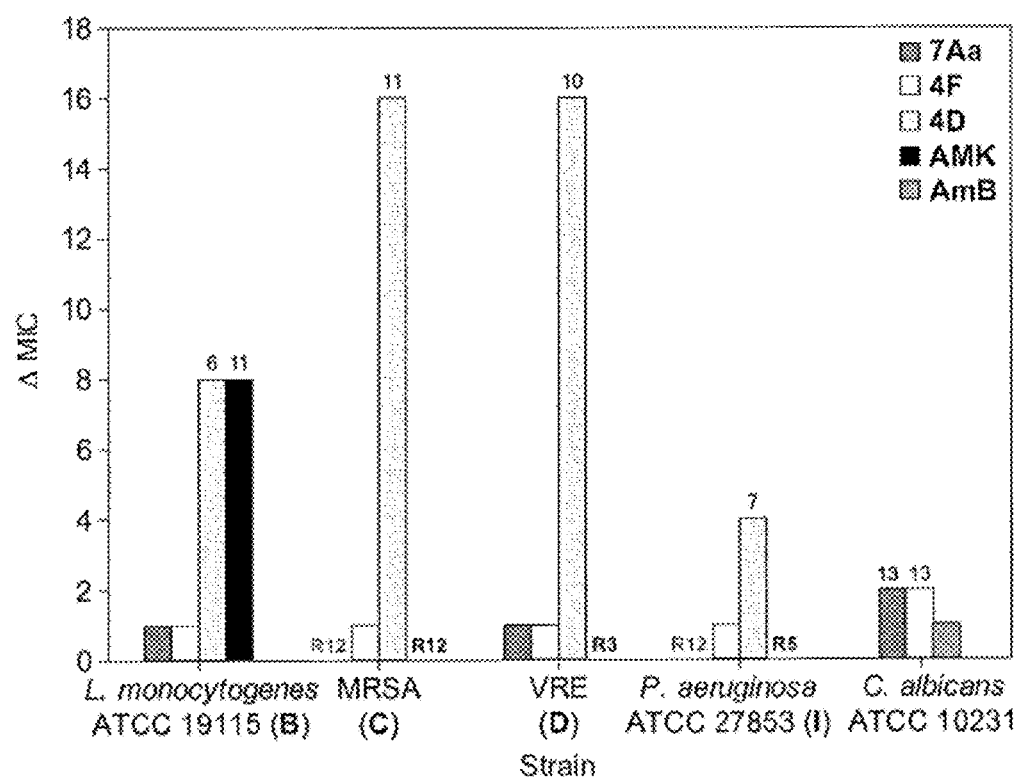
FIG. 2 is a bar graph showing the changes in MIC values of *L. monocytogenes* ATCC 19115 (strain B), MRSA (strain C), VRE (strain D), and *P. aeruginosa* ATCC 27853 (strain I) treated previously with AMK (green), 7Aa (purple), 4F (blue), 4D (orange), as well as *C. albicans* ATCC 10231 treated previously with AmB (yellow), 7Aa (purple), and 4F (blue) over 15 cycles. Numbers above the bars represent the passage number when either bacterial or fungal cells developed resistance.

To establish if the bis(N-amidino)hydrazones and N-amidino-N-aryl-bishydrazones evaded resistance in bacteria, a multi-step resistance selection experiment was performed with compounds 4D, 4F, and 7Aa and with AMK as a reference drug against four bacterial strains (FIG. 2). *L. monocytogenes* ATCC 19115 (strain B), MRSA (strain C), VRE (strain D), and *P. aeruginosa* ATCC 27853 (strain I) were exposed to sub-inhibitory concentrations of compounds 4D, 4F, 7Aa, and AMK, and were sub-cultured for 15 serial passages to determine if any increase in MIC values occurred for each compounds against the strains tested. *L. monocytogenes* ATCC 19115 (strain B), MRSA (strain C), VRE (strain D), and *P. aeruginosa* ATCC 27853 (strain I) did not develop resistance to compound 4F, as established by the fact that the relative MIC values increased only by one-fold after 15 serial passages. Likewise, strains B and D did not develop resistance to compound 7Aa, but strains C and I developed resistance to this compound after 15 serial passages. In contrast, the rapid development of resistance to compound 4D was observed in strains C and D with a 16-fold increase in MIC values after fifteen serial passages. This resistance development against compound 4D was also observed in strains B and I, where increases in relative MIC values by 8- and 4-folds were observed after 15 passages. Interestingly, in strains D and I, resistance to the control antibiotic, AMK, was also observed after 3 and 5 passages, respectively, whereas in strains C and B, resistance developed after 12 and 15 passages, respectively. Overall, these results indicate that there is a low probability of emergence of resistance to the antifungal, biscationic compounds 4F and 7Aa.

The potential development of drug resistance in *C. albicans* ATCC 10231 to antifungal compounds 7Aa and 4F was investigated. The results indicated that *C. albicans* ATCC 10231 was unable to develop drug resistance to either 7Aa or 4F, despite repeated treatments with sub-MIC drug concentrations. Only a slight 2-fold shift in relative MIC values was observed after 13 passages. These results also suggested the appearance of drug resistance by fungi to the antifungal compounds of the present disclosure is highly unlikely, a particularly desirable outcome.

Measurement of ROS Induction in Fungal Cells

Various antifungal drugs, such as AmB and miconazole, as well as the antifungal agents of the present disclosure, were shown to mediate their inhibitory effect by inducing intracellular ROS production. Universally, eukaryotic cells produce basal amount of ROS in mitochondria as a byproduct of cellular metabolism. In response, the cellular enzymatic antioxidants, including superoxide dismutase and glutathione peroxidase, scavenge ROS in cells. However, overproduction of deleterious ROS perturbs the delicate, intracellular equilibrium between ROS production and scavenging, and results in cellular damage.

Figure 3:
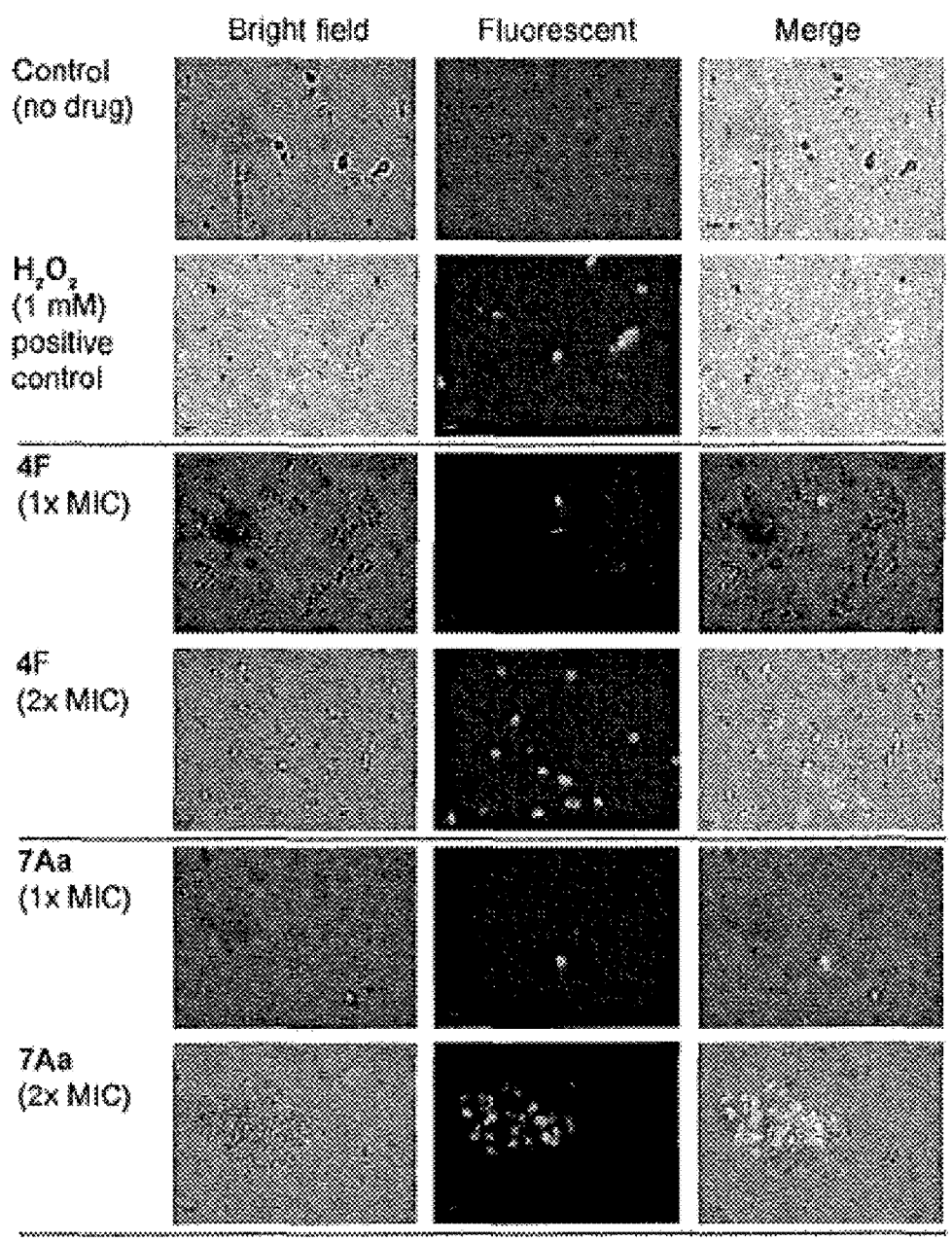
FIG. 3 shows images illustrating the effect of compounds 4F and 7Aa on intracellular ROS production by *C. albicans* ATCC 10231. Yeast cells were treated with no drug (negative control), 1 mM of H$_2$O$_2$ (positive control), or 4F and 7Aa, at their 1× and 2× respective MIC values for 1 h at 35° C. After staining with DCFH-DA (20 μg/mL), the samples were analyzed using a Zeiss Axovert 200M fluorescence microscope.

To show the ability of compounds 4F and 7Aa to alter ROS production in *C. albicans* ATCC 10231 (strain A), a fluorescent-based assay was performed using a 2',7'-dichlorodihydrofluorescein diacetate (DCFH-DA) dye. It was found that treatment of *C. albicans* ATCC 10231 (strain A) with compounds 4F and 7Aa at their 1× and 2×MIC values significantly increased intracellular ROS production in this fungal strain (FIG. 3). As expected, an $H_2O_2$ positive control (at 1 mM) also induced ROS production in yeast cell, whereas no ROS induction was observed with untreated yeast cells (negative control).

Cytotoxicity

Figure 4A:
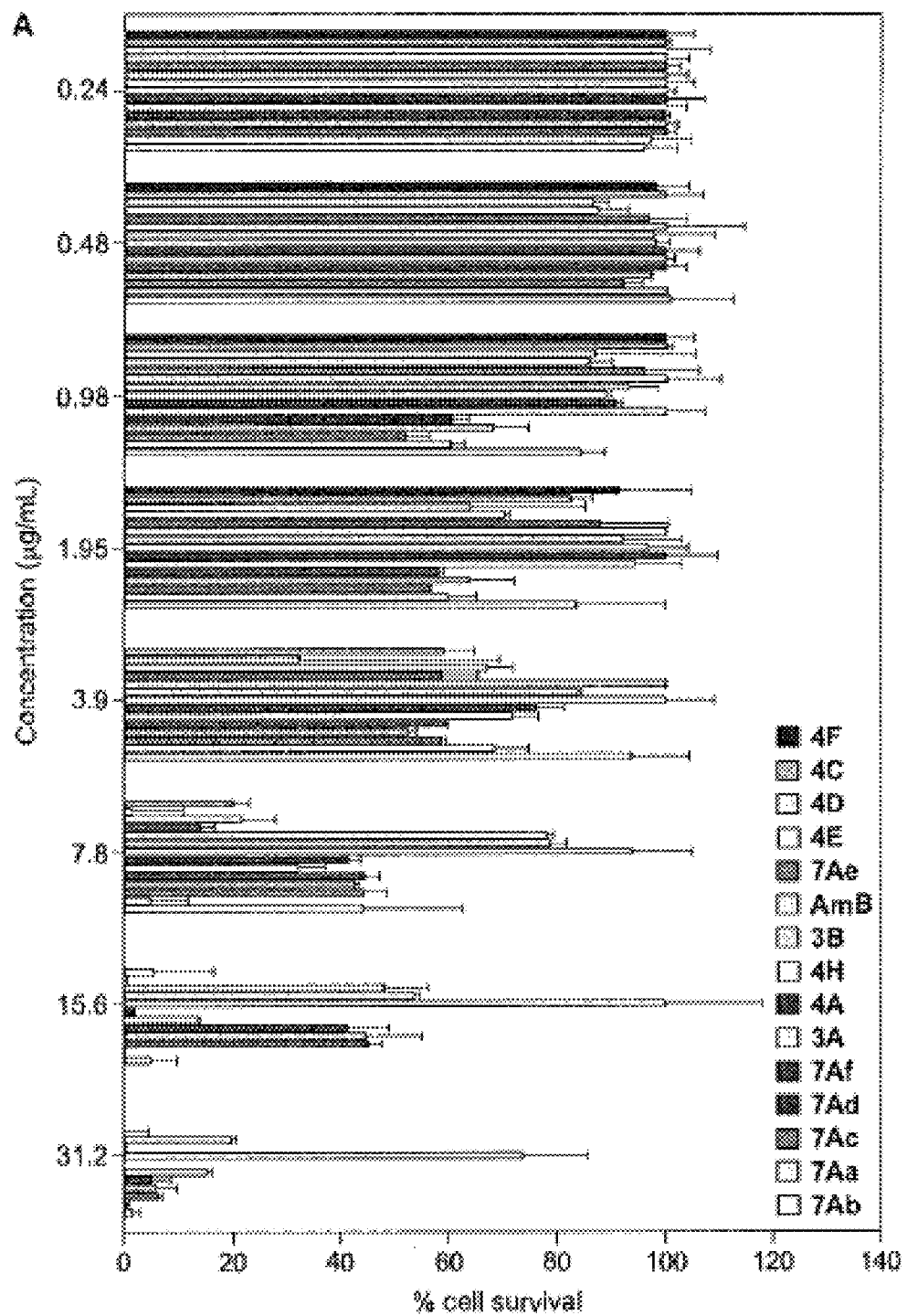
FIGS. 4A-B show graphs illustrating a mammalian cell cytotoxicity of selected bis(N-amidino)hydrazones and N-amidino-N-aryl-bishydrazones, as well as AmB (as a control) against (A) A549 cell line and (B) BEAS-2B cell line.
Figure 4B:
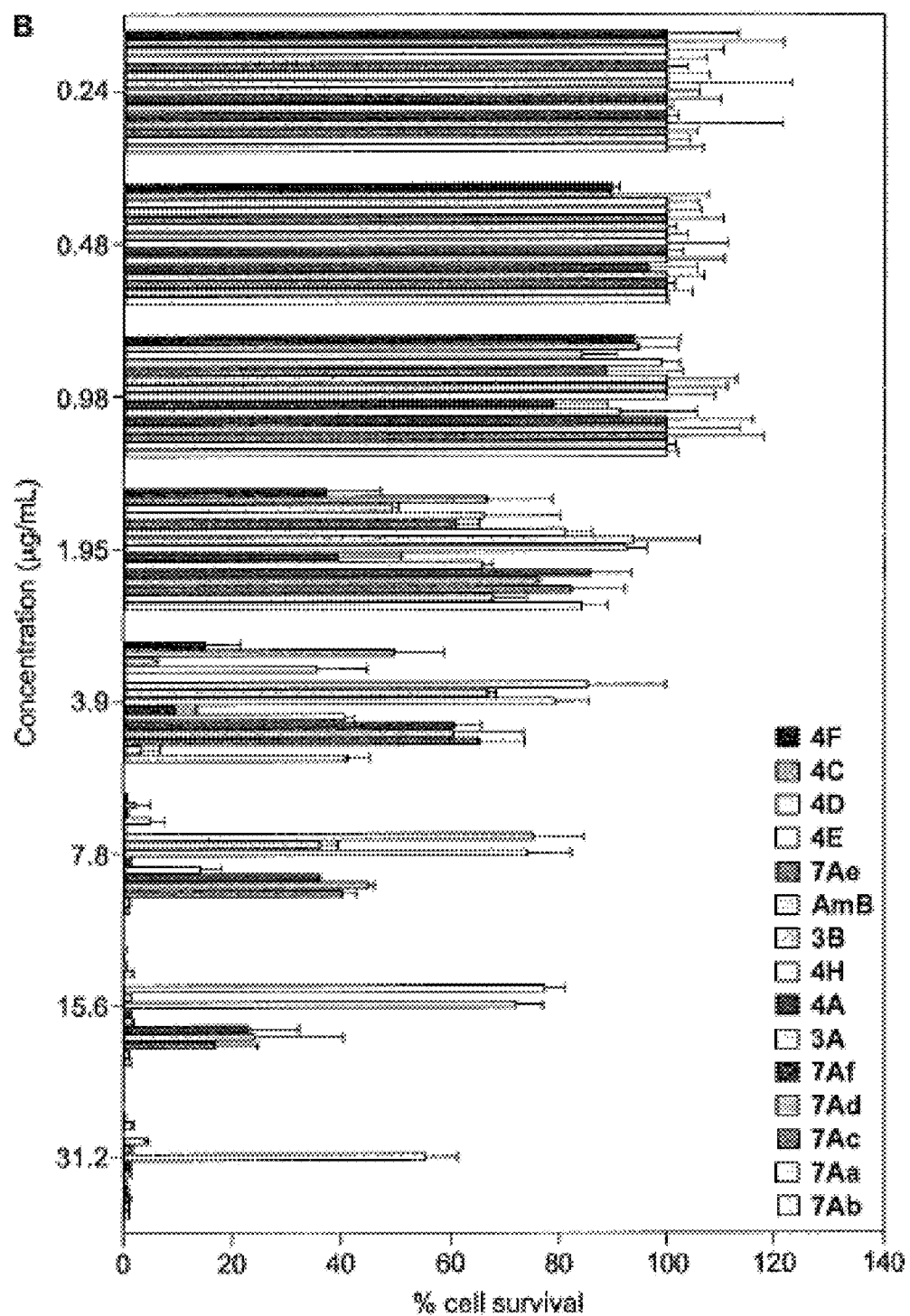

Another important aspect to consider during the development of antimicrobial agents is their potential toxicity towards mammalian cells. Having established the potent antimicrobial activities of the bis(N-amidino)hydrazones and N-amidino-N'-aryl-bishydrazones against bacteria and fungi, the toxicity profile of these compounds was determined against two mammalian cell lines (A549 and BEAS-2B; FIGS. 4A-B). The majority of the compounds showed dose-dependent toxicity with $IC_{50}$ values of 1.95-3.9 μg/mL against these cell lines. Compounds 3B, 7Ac, 7Ad, and 7Af with antibacterial MIC values of <0.4-3.3 μg/mL, displayed good $IC_{50}$ values of 7.8-15.6 μg/mL against both mammalian cell lines. It is important to remember that compounds 7Ac and 7Af also displayed strong antifungal MIC values.

hERG Inhibition Assay

The human Ether-a-go-go related gene (hERG) encodes a voltage-gated potassium channel that plays an essential role in regulating heart rhythm. Inhibition of the potassium channel coded by hERG disrupts the heart rhythm and may lead to death. Recently, clinically used drugs (e.g., terfendadine and cisapride) were withdrawn from the market due to their interaction with hERG. Currently, the U.S. Food and Drug Administration (FDA) and the European Medicines Agency (EMA) require testing of hERG affinity for potential novel drugs during the early stage of the drug development.

Figure 5:
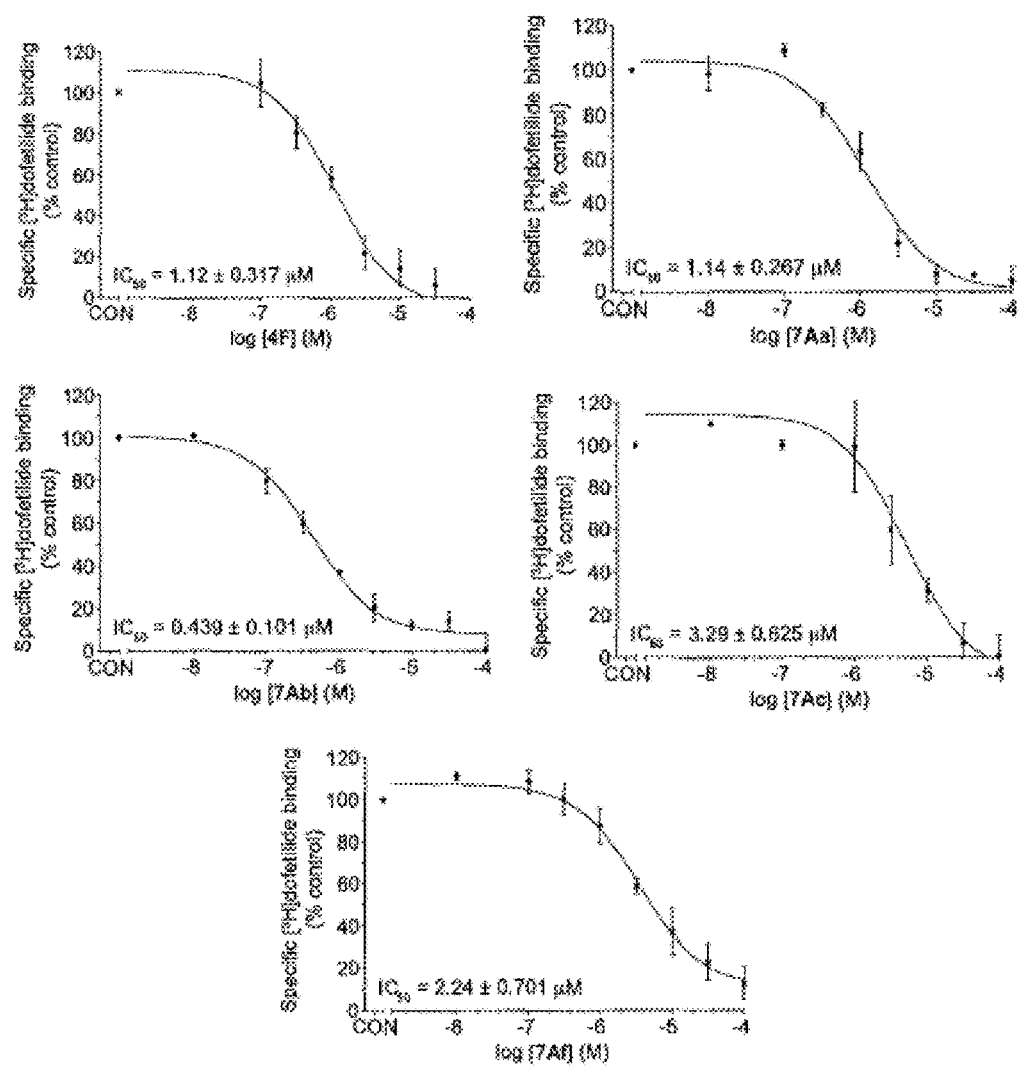
FIG. 5 shows graphs illustrating IC$_{50}$ curves for hERG inhibition by some representative bis(N-amidino)hydrazones and N-amidino-N-aryl-bishydrazones.

A [$^3$H]-dofetilide competition binding assay using HEK-293 cell membranes stably expressing hERG channel was performed to evaluate interaction of the most potent bis(N-amidino)hydrazones and N-amidino-N'-aryl-bishydrazones with hERG (FIG. 5). Compounds exhibiting $IC_{50}$ values of >10 μM are considered to have desirable, low affinity for the hERG channel. Compounds displaying $IC_{50}$ values in the range of 1-10 μM are considered moderate inhibitors, whereas compounds exhibiting $IC_{50}$ values of <1 μM are considered to have undesirable, high affinity for the hERG channel. The majority of the compounds of the present disclosure displayed $IC_{50}$ values within the acceptable range of 1-10 μM (FIG. 5) against the hERG channel. For example, the p-fluorophenyl and the 2,4-difluorophenyl groups in compounds 7Ac and 7Af displayed only moderate inhibition of the hERG channel with $IC_{50}$ values of 3.29±0.625 μM and 2.24±0.701 μM, respectively. Strikingly, both of these compounds displayed excellent antifungal activities and also exerted low mammalian cell toxicity. Similarly, compounds 4F and 7Aa also displayed moderate inhibition of hERG channel with IC$_{50}$ values of 1.12±0.317 µM and 1.14±0.267 µM, respectively; however, they displayed some toxicity against mammalian cells. Therefore, it was concluded, once again, that compounds 7Ac and 7Af are the most promising N-amidino-N'-aryl-bishydrazones.

Example 2

Materials and Instrumentation.

Chemicals were purchased from Sigma-Aldrich-Fluka (PO Box 14508 St. Louis, Mo., 63178, USA), Matrix, Inc. (131 Pontiac Business Center Dr., Elgin, S. C., 29045, USA), and Thermo-Scientific (7383 Empire Dr., Florence, Key., 41042, USA), or were synthesized according to literature procedures, unless otherwise noted. Solvents were used from commercial vendors without further purification unless otherwise noted. Nuclear magnetic resonance (NMR) spectra were determined in DMSO-d$_6$ using an Agilent 400 series NMR instrument. The DMSO center line was set as the reference at 2.5 ppm for $^1$H NMR spectra and at 39.51 ppm for $^{13}$C NMR spectra. LRMS electron-impact (EI) ionization mass spectra were recorded at 70 eV on a ThermoFinnigan PolarisQ (ion trap mass spectrometer). Samples were introduced via a heatable direct probe inlet. High-resolution electron impact (EI) ionization mass spectra were recorded at 25 eV on a JEOL JMS-700T MStation (magnetic sector instrument) at a resolution of greater than 10,000. Samples were introduced via heatable direct probe inlet. MALDI mass spectra were obtained on a Bruker Utraflexstreme time-of-flight mass spectrometer (Billerica, Mass.), using DHB (2,5-dihydroxybenzoic acid) matrix. Purity of compounds was >95% as established by combustion analyses. In the case of compounds that resisted crystallization or were too valuable to sacrifice to combustion, purity was established by a combination of high-resolution mass spectra and $^{13}$C NMR data. Elemental analyses were determined by Atlantic Microlabs, Inc. (6180 Atlantic Blvd # M, Norcross, Ga., 30071, USA). Compounds were chromatographed on preparative layer Merck silica gel F254 or columns using MP Silica 63-200, 60 Å, MP EcoChrom (Eschwege, Germany). Organic solutions were dried over anhydrous MgSO$_4$ unless otherwise noted.

Experimental Procedures and Characterization of Compounds 3A-8Aa:

General Procedure for the Synthesis of Aryl Bis[N-(Guanidino)Imines] 3A-4H.

To a solution of aminoguanidine hydrochloride (2 mmol, 2 eq) in 3 mL of absolute EtOH at 78° C. was added 1 mmol (1 eq) of bisaldehyde 1 (R=H) or bisketone 2 (R=CH$_3$) and 10 µL of concentrated HCl. The mixture was heated for 2 h and cooled to 0° C. The resulting white solid was filtered and washed with 2 mL of cold EtOH to afford aryl N-(guanidino) imines 3A-B and 4A,C-H as dihydrochloride salts.

Characterization of Compounds 3A-B and 4A,C-H:

(2E,2'E)-2,2'-([1,1'-Biphenyl]-4,4'-diylbis(methanylylidene))bis(hydrazine-1-carboximidamide) dihydrochloride[1] (3A)

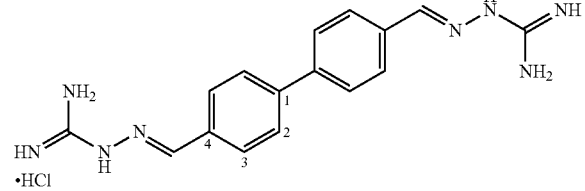

CAS: 109501-35-1. Yield: 86%; mp 340-342° C. $^1$H NMR (400 MHz, DMSO-d$_6$) δ 7.84 (d, J=8.4 Hz, 4H, H-2), 7.85 (br s, 8H, CH=NNHC(NH$_2$)=NH$_2^+$), 7.98 (d, J=8.4 Hz, 4H, H-3), 8.24 (s, 2H, CH=NNHC(NH$_2$)=NH$_2^+$), 11.8 (br s, 2H, CH=NNHC(NH$_2$)=NH$_2^+$). $^{13}$C NMR (100 MHz, DMSO-d$_6$) δ 127.0 (C-2), 128.2 (C-3), 133.0 (C-1), 140.9 (C-4), 146.3 (CH=NNHC(NH$_2$)=NH$_2^+$), 155.4 (CH=NNHC(NH$_2$)=NH$_2^+$). HRMS (nEI) Calcd. for C$_{16}$H$_{21}$Cl$_2$N$_8$ [M+H]$^+$: 323.1727. Found: 323.1727. Anal. Calcd. for C$_{16}$H$_{20}$Cl$_2$N$_8$: C, 48.62; H, 5.10; N, 28.35. Found: C, 48.72; H, 5.01; N, 28.20.

(2E,2'E)-2,2'-([1,1'-Biphenyl]-3,4'-diylbis(methanylylidene))bis(hydrazine-1-carboximidamide) dihydrochloride (3B)

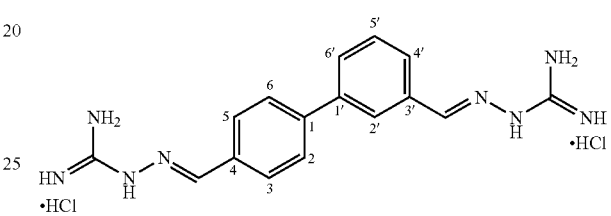

Yield: 73%; mp 368-370° C. $^1$H NMR (400 MHz, DMSO-d$_6$) δ 7.53 (t, J=8.0 Hz, 1H, H-5'), 7.78-7.85 (m, 4H, H-2, H-4', H-6 and H-6'), 7.96 (d, J=8.4 Hz, 2H, H-3 and H-5), 7.2-8.5 (br s, 8H, CH=NNHC(NH$_2$)=NH$_2^+$), 8.21 (s, 1H, CH=NNHC(NH$_2$)=NH$_2^+$), 8.22 (br s, 1H, H-2'), 8.23 (s, 1H, CH=NNHC(NH$_2$)=NH$_2^+$), 12.1 (br s, 2H, CH=NNHC(NH$_2$)=NH$_2^+$). $^{13}$C NMR (100 MHz, DMSO-d$_6$) δ 125.6 (C-2'), 127.1 (C-2 and C-6), 127.2 (C-6'), 128.2 (C-3 and C-5), 128.8 (C-4'), 129.4 (C-5'), 132.9 (C-1'), 134.2 (C-1), 139.8 (C-3'), 141.2 (C-4), 146.4 (CH=NNHC(NH$_2$)=NH$_2^+$), 146.6 (CH=NNHC(NH$_2$)=NH$_2^+$), 155.4 (CH=NNHC(NH$_2$)=NH$_2^+$), 155.5 (CH=NNHC(NH$_2$)=NH$_2^+$). HRMS (nEI) Calcd. for C$_{12}$H$_{19}$N$_8$ [M+H]$^+$: 275.1727. Found: 275.1726.

(2E,2'E)-2,2'-([1,1'-Biphenyl]-4,4'-diylbis(ethan-1-yl-1-ylidene))bis(hydrazine-1-carboximidamide) dihydrochloride[2] (4A)

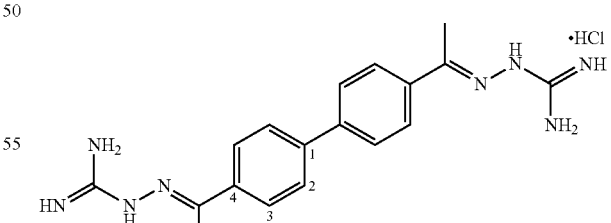

CAS: 5961-64-8. Yield: 80%; mp >380° C. $^1$H NMR (400 MHz, DMSO-d$_6$) δ 2.4 (s, 6H, C(CH$_3$)=NNHC(NH$_2$)=NH$_2^+$), 7.78 (d, J=8.4 Hz, 4H, H-2), 7.9 (br s, 8H, C(CH$_3$)=NNHC(NH$_2$)=NH$_2^+$), 8.07 (d, J=8.4 Hz, 4H, H-3), 11.4 (br s, 2H, C(CH$_3$)=NNHC(NH$_2$)=NH$_2^+$). $^{13}$C NMR (100 MHz, DMSO-d$_6$) δ 14.7 (C(CH$_3$)=NNHC(NH$_2$)=NH$_2^+$), 126.5 (C-2), 127.4 (C-3), 136.2 (C-1), 140.3 (C-4), 151.2 (C(CH₃)=NNHC(NH₂)=NH₂⁺), 156.1 (C(CH₃)=NNHC(NH₂)=NH₂⁺). HRMS (nEI) Calcd. for C₁₈H₂₃N₈ [M+H]⁺: 351.2040. Found: 351.2040. Anal. Calcd. for C₁₈H₂₄Cl₂N₈: C, 51.07; H, 5.71; N, 26.47. Found: C, 51.15; H, 5.68; N, 26.37.

(2E,2'E)-2,2'-((methylenebis(4,1-phenylene))bis(ethan-1-yl-1-ylidene))bis(hydrazine-1-carboximidamide) dihydrochloride (4C)

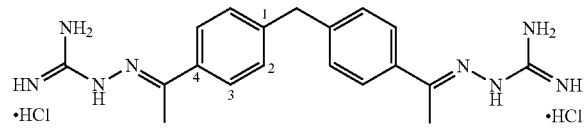 [SMILES: Cl ; C/C(=N\NC(=N)N)c1ccc(Cc2ccc(/C(C)=N/NC(=N)N)cc2)cc1 ; Cl]

Yield: 91%; mp 342-344° C. ¹H NMR (400 MHz, DMSO-d₆) δ 2.32 (s, 6H, C(CH₃)=NNHC(NH₂)=NH₂⁺), 4.02 (s, 2H, ArCH₂Ar), 7.28 (d, J=8.4 Hz, 4H, H-2), 7.81 (br s, 8H, C(CH₃)=NNHC(NH₂)'NH₂⁺), 7.87 (d, J=8.4 Hz, 4H, H-3), 11.3 (br s, 2H, C(CH₃)=NNHC(NH₂)=NH₂⁺). ¹³C NMR (100 MHz, DMSO-d₆) δ 14.6 (C(CH₃)=NNHC(NH₂)=NH₂⁺), 40.4 (ArCH₂Ar), 126.9 (C-2), 128.6 (C-3), 134.8 (C-1), 142.8 (C-4), 151.5 (C(CH₃)=NNHC(NH₂)=NH₂⁺), 156 (C(CH₃)=NNHC(NH₂)=NH₂⁺). HRMS (nEI) Calcd. for C₁₉H₂₅N₈ [M+H]⁺: 365.2197. Found: 365.2197. Anal. Calcd. for C₁₉H₂₆Cl₂N₈: C, 52.18; H, 5.99; N, 25.62. Found: C, 51.85; H, 5.95; N, 25.31.

(2E,2'E)-2,2'-((Ethane-1,2-diylbis(4,1-phenylene))bis(ethan-1-yl-1-ylidene))bis(hydrazine-1-carboximidamide) dihydrochloride³ (4D)

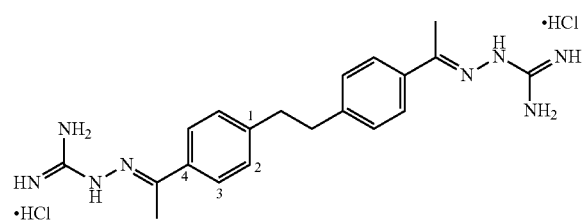 [SMILES: Cl ; C/C(=N\NC(=N)N)c1ccc(CCc2ccc(/C(C)=N/NC(=N)N)cc2)cc1 ; Cl]

CAS: 5265-92-9. Yield: 66%; mp >380° C. ¹H NMR (400 MHz, DMSO-d₆) δ 2.33 (s, 6H, C(CH₃)=NNHC(NH₂)=NH₂⁺), 2.94 (s, 4H, Ar(CH₂)₂Ar), 7.25 (d, J=8.4 Hz, 4H, H-2); 7.81 (br s, 8H, C(CH₃)=NNHC(NH₂)=NH₂⁺), 7.86 (d, J=8.4 Hz, 4H, H-3), 11.25 (br s, 2H, C(CH₃)=NNHC(NH₂)=NH₂⁺). ¹³C NMR (100 MHz, DMSO-d₆) δ 14.6 (C(CH₃)=NNHC(NH₂)=NH₂⁺), 36.3 (Ar(CH₂)₂Ar), 126.7 (C-2), 128.4 (C-3), 134.5 (C-1), 143.1 (C-4), 151.6 (C(CH₃)=NNHC(NH₂)=NH₂⁺), 156.0 (C(CH₃)=NNHC(NH₂)=NH₂⁺). HRMS (nEI) Calcd. for C₂₀H₂₇N₈ [M+H]⁺: 379.2352. Found: 379.2352. Anal. Calcd. for C₂₀H₂₈Cl₂N₈: C, 53.22; H, 6.25; N, 24.82. Found: C, 52.93; H, 6.09; N. 25.05.

(2E,2'E)-2,2'-((Oxybis(4,1-phenylene))bis(ethan-1-yl-1-ylidene))bis(hydrazine-1 carboximidamide), dihydrochloride⁴ (4E)

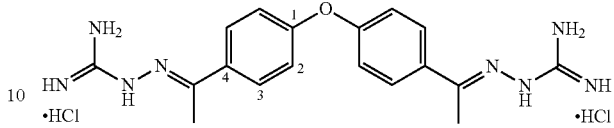

CAS: 17027-93-9. Yield: 73%; mp 340-342° C. ¹H NMR (400 MHz, DMSO-d₆) δ 2.35 (s, 6H, C(CH₃)=NNHC(NH₂)=NH₂⁻), 7.08 (d, J=8.4 Hz, 4H, H-2), 7.74 (br s, 8H, C(CH₃)=NNHC(NH₂)=NH₂⁺), 8.02 (d, J=8.4 Hz, 4H, H-3), 11.0 (br s, 2H, C(CH₃)=NNHC(NH₂)=NH₂⁺). ¹³C NMR (100 MHz, DMSO-d₆) δ 14.6 (C(CH₃)=NNHC(NH₂)=NH₂⁺), 118.3 (C-2), 128.8 (C-3), 132.4 (C-4), 150.9 (C(CH₃)=NNHC(NH₂)=NH₂⁺), 156 (C-1), 157.5 (C(CH₃)=NNHC(NH₂)=NH₂⁺). HRMS (nEI) Calcd. for C₁₈H₂₃N₈O [M+H]⁺: 367.1989. Found: 367.1987. Anal. Calcd. for C₁₈H₂₄Cl₂N₈O: C, 49.21; H, 5.51; N, 25.51. Found: C, 49.12; H, 5.53; N, 25.43.

(2E,2'E)-2,2'-((9H-Fluorene-2,7-diyl)bis(ethan-1-yl-1-ylidene))bis(hydrazine-1-carboximidamide) dihydrochloride (4F)

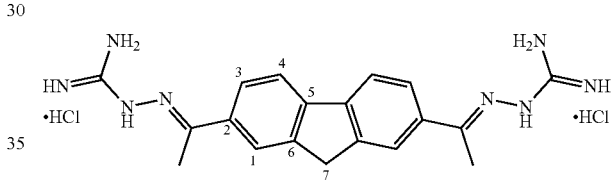

CAS: 63956-03-6, NCI 304392. Yield: 96%; mp >380° C. ¹H NMR (400 MHz, DMSO-d₆) δ 2.42 (s, 6H, C(CH₃)=NNHC(NH₂)=NH₂⁺), 4.01 (s, 2H, H-7), 7.88 (br s, 8H, C(CH₃)=NNHC(NH₂)=NH₂⁺), 8.01 (d, J=8.4 Hz, 2H, H-4), 8.03 (d, J=8.4 Hz, 2H, H-3), 8.24 (s, 2H, H-1), 11.33 (br s, 2H, C(CH₃)=NNHC(NH₂)=NH₂⁺). ¹³C NMR (100 MHz, DMSO-d₆) δ 14.8 (C(CH₃)=NNHC(NH₂)=NH₂⁺), 36.5 (C-9), 120.3 (C-4), 123.6 (C-1), 125.9 (C-3), 135.8 (C-6), 141.9 (C-5), 143.8 (C-2), 151.8 (C(CH₃)=NNHC(NH₂)=NH₂⁺), 156.1 (C(CH₃)=NNHC(NH₂)=NH₂⁺). HRMS (nEI) Calcd. for C₁₉H₂₃N₈ [M+H]⁺: 363.2040. Found: 363.2039. Anal. Calcd. for C₁₉H₂₄Cl₂N₈·½H₂O: C, 51.36; H, 5.67; N, 25.22. Found: C, 51.19; H, 5.59; N, 25.06. ½.

(2E,2'E)-2,2'-(1,4-Phenylenebis(ethan-1-yl-1-ylidene))bis(hydrazine-1-carboximidamide) dihydrochloride⁴ (4G)

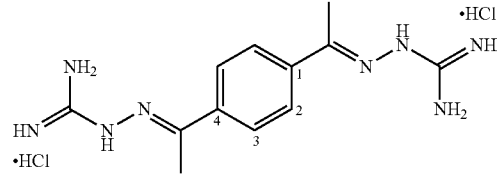 [SMILES: Cl ; C/C(=N\NC(=N)N)c1ccc(/C(C)=N/NC(=N)N)cc1 ; Cl]

CAS: 2299-94-7. Yield: 97%; mp>380° C. $^1$H NMR (400 MHz, DMSO-d$_6$) δ 2.38 (s, 6H, C(CH$_3$)=NNHC(NH$_2$$^+$)=NH$_2$$^+$), 7.87 (br s, 8H, C(CH$_3$)=NNHC(NH$_2$)=NH$_2$$^-$), 7.99 (s, 4H, H-2, H-3), 11.3 (br s, 2H, C(CH$_3$)=NNHC(NH$_2$)=NH$_2$$^+$). $^{13}$C NMR (100 MHz, DMSO-d$_6$) δ 14.7 (ArC(=NNHR)CH$_3$), 126.6 (C-2, C-3, C-5, and C-6), 137.8 (C-1 and C-4), 151.1 (Ar C(=NNHR)CH$_3$), 156.067 (NHC(NH$_2$)=NH$_2$$^+$). HRMS (nEI) Calcd. for C$_{12}$H$_{19}$N$_8$ [M+H]$^+$: 275.1727. Found: 275.1726. Anal. Calcd. for C$_{12}$H$_{20}$Cl$_2$N$_8$·½H$_2$O: C, 40.46; H, 5.94; N, 31.45. Found: C, 40.68; H, 6.10; N, 31.26.

(2E,2'E)-2,2'-(1,3-Phenylenebis(ethan-1-yl-1-ylidene))bis(hydrazine-1-carboximidamide) dihydrochloride$^6$ (411)

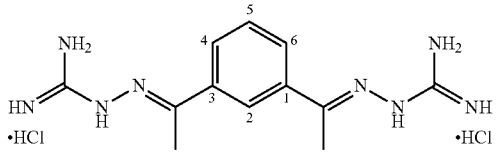 [SMILES: Cl ; C/C(=N\NC(=N)N)c1cccc(/C(C)=N/NC(=N)N)c1 ; Cl]

CAS: 87533-31-1. Yield: 86%; mp 330-332° C. $^1$H NMR (400 MHz, DMSO-d$_6$) δ 2.42 (s, 6H, C(CH$_3$)=NNHC(NH$_2$)=NH$_2$$^+$), 7.47 (t, J=8.0 Hz, 1H, H-5), 7.87 (br s, 8H, C(CH$_3$)=NNHC(NH$_2$)=NH$_2$$^+$), 8.03 (dd, J=8.0 and 2.0 Hz, 2H, H-4 and H-6), 8.26 (t, J=2.0 Hz, 1H, H-2), 11.34 (br s, 2H, C(CH$_3$)=NNHC(NH$_2$)=NH$_2$$^+$). $^{13}$C NMR (100 MHz, DMSO-d$_6$) δ 15.0 (CH$_3$), 124.8 (C-5), 128.0 (C-4 and C-6), 128.4 (C-2), 137.1 (C-1 and C-3), 151.7 C(CH$_3$)=NNHC(NH$_2$)=NH$_2$$^+$), 156.2 (C(CH$_3$)=NNHC(NH$_2$)=NH$_2$$^+$). HRMS (nEI) Calcd. for C$_{12}$H$_{19}$N$_8$ [M+H]$^+$: 257.1727. Found: 275.1726. Anal. Calcd. for C$_{12}$H$_{20}$Cl$_2$N$_8$: C, 41.51; H, 5.81; N, 32.27. Found: C, 41.27; H, 5.71; N, 32.13.

General Procedure for the Synthesis of Aryl N-(Guanidino)Imines N'-Arylhydrazones 7Aa-Ag and 8Aa.

To 40.5 mmol (3 eq) of a bis(aldehyde) 1A (R=H) or bis(ketone) 2A (R=CH$_3$) in 20 mL of absolute EtOH at 78° C. was added dropwise a solution of 1.5 g (13.5 mmol, 1 eq) of aminoguanidine hydrochloride in 80 mL of 1:15/H$_2$O: EtOH. To this solution was added 2 mL of concentrated HCl, and the mixture was heated for an additional 12 h. The mixture was concentrated under vacuum to afford a solid. The solid was heated with ca. 10 mL of EtOAc to dissolve any unreacted dicarbonyl compound, as confirmed by TLC of the undissolved solid using 1:50/MeOH:CH$_2$Cl$_2$. After decanting the EtOAc solution, the remaining white precipitate consisted of the monosubstituted N-(guanidino)imine 5A and 6A that was used directly in the next step. To 113 mg (0.5 mmol, 1 eq) of 5A or 6A suspended in 2 mL of absolute EtOH at 78° C. was added 0.5 mmol (1 eq) of an aryl hydrazine followed by 0.02 mL of concentrated HCl. A clear solution was produced by the addition of acid, and within 15-30 min, a precipitate was formed. The mixture was heated at 78° C. for 24 h, and the precipitate was collected by filtration of the hot mixture. The precipitate was washed cold absolute EtOH to yield >95% of pure unsymmetrical aryl N-(guanidino)imines N'-arylhydrazones 7Aa-Ag and 8Aa.

Characterization of Compounds 7Aa-Ag and 8Aa:

E)-2-((4'-((E and Z)-(2-(2-Chlorophenyl)hydrazono)methyl)-[1,1'-biphenyl]-4-yl)methylene)hydrazine-1-carboximidamide monohydrochloride (7Aa)

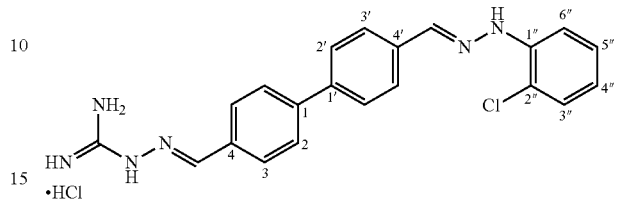

Yield: 70%; mp 328-330° C. $^1$H NMR, (400 MHz, DMSO-d$_6$) δ 6.81 (dt, J=8.4 and 1.6 Hz, 1H, H-4"), 7.28 (dt, J=7.6 and 1.2 Hz, 1H, H-5"), 7.34 (dd, J=8.0 and 1.6 Hz, 1, H-3"), 7.6 (dd, J=8.4 and 1.2 Hz, 1H, H-6"), 7.75-7.80 (m, 4H, H-2 and H-2'), 7.80 and 7.84 (two d, J=8.4 Hz, 1H, 45:55 ratio of syn:anti H-3'), 7.97 and 7.98 (two d, J=8.4 Hz, 1H, 45:55 ratio of syn:anti H-3), 8.23 and 8.234 (two s, 1H, 45:55 ratio of syn:anti CH=NNHAr), 8.34 (s, 1H, CH=NNHC(NH$_2$)=NH$_2$$^+$), 9.98 and 10 (two br s, 1H, 55:45 ratio of anti:syn CH=NNHAr), 12.03 and 12.08 (two br s, 1H, 45:55 ratio of syn:anti CH=NN HC(NH$_2$)=NH$_2$$^+$). $^{13}$C NMR (100 MHz, DMSO-d$_6$) δ 114.1 (C-2"), 116.23 and 116.3 (anti:syn C-6"), 119.7 and 119.8 (anti:syn C-4"), 126.6 and 126.8 (anti:syn C-2'), 126.6 and 126.8 (anti:syn C-3'), 126.7 and 126.8 (syn:anti C-2), 127 and 127.1 (anti:syn C-3), 128.1 and 128.3 (syn:anti C-3'), 129.4 (C-3"), 132.7 and 133 (syn:anti C-1'), 134.7 and 135.1 (anti:syn C-1), 139.1 and 139.4 (anti:syn C-4'), 139.8 and 139.9 (syn:anti C-4'), 140.9 and 141.3 (syn:anti C-1'), 141.33 and 141.3 (syn:anti CH=NNHC(NH$_2$)=NH$_2$$^+$), 146.3 and 146.4 (anti:syn CH=NNHAr), 155.38 and 155.4 (syn:anti CH=NNHC(NH$_2$)=NH$_2$$^+$). HRMS (nEI) Calcd. for C$_{21}$H$_{20}$N$_6$Cl [M+H]$^+$: 391.1432. Found: 391.1431. Anal. Calcd. for C$_{21}$H$_{20}$C$_{12}$N$_6$·½H$_2$O: C, 57.81; H, 4.85; N, 19.26. Found: C, 58.46; H, 4.69; N, 19.27.

(E)-2-((4'-((E and Z)-(2-(2-Bromophenyl)hydrazono)methyl)-[1,1'-biphenyl]-4-yl)methylene)hydrazine-1-carboximidamide monohydrochloride (7Ab)

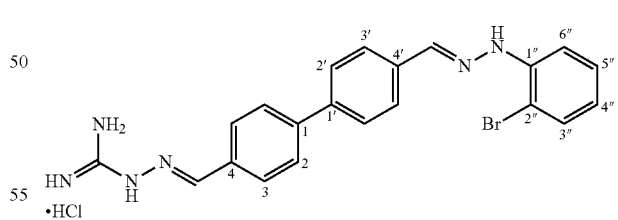

Yield: 64%; mp >380° C. $^1$H NMR (400 MHz, DMSO-d$_6$) δ 6.75 (dt, J=8.4 and 1.6 Hz, 1H, H-4"), 7.32 (dt, J=7.6 and 1.2 Hz, 1H, H-5"), 7.5 (dd, J=8.0 and 1.6 Hz, 1H, H-3"), 7.58 (dd, J=8.4 and 1.2 Hz, 1H, H-6"), 7.75-7.85 (m, 6H, H-2, H-2', and H-3'), 7.80 (br s, 4H, CH=NNHC(NH$_2$)=NH$_2$$^+$), 7.97 and 7.98 (two d, J=8.4 Hz, 1H, 45:55 ratio of syn:anti H-3), 8.227 and 8.232 (two s, 1H, 45:55 ratio of syn:anti C H=NNHAr), 8.364 (s, 1H, CH=NNHC(NH$_2$)=NH$_2$$^+$), 9.74 and 9.75 (two br s, 1H, 45:55 ratio of anti:syn CH=NN HAr), 11.97 and 12.03 (two br s, 1H, 45:55 ratio of syn:anti CH=NNHC(NH₂)=NH₂⁺). ¹³C NMR (100 MHz, DMSO-d₆) δ 106.1 and 106.2 (anti:syn C-2″), 114.6 (C-6″), 120.4 and 120.5 (anti:syn C-4″), 126.66 and 126 72 (anti:syn C-2), 126.7 and 127 (anti:syn C-3′), 126.8 and 127.1 (anti:syn C-2′), 128.3 (C-3), 128.6 (C-5″), 132.6 (C-1′), 132.6 and 133 (anti:syn C-3″), 134.7 and 135.1 (anti:syn C-1), 139.1 and 139.4 (anti:syn C-4″), 140 and 140.1 (syn:anti C-4), 141 and 141.3 (anti:syn C-1″), 142.34 and 142.38 (syn:anti CH=NNHC(NH₂)=NH₂⁺), 146.4 and 146.5 (syn:anti CH=NNHAr), 155.34 and 155.36 (syn:anti CH=NNHC(NH₂)=NH₂⁺). HRMS (nEI) Calcd. for C₂₁H₁₉BrN₆ [M+H]⁺: 435.0927. Found: 435.0928. Anal. Calcd. for C₂₁H₂₀BrClN₆: C, 53.46; H, 4.27; N, 17.81. Found: C, 53.10; H, 4.29; N, 17.19.

(E)-2-((4′-((E)-(2-(4-Fluorophenyl)hydrazono) methyl)-[1,1′-biphenyl]-4-yl)methylene)hydrazine-1-carboximidamide monohydrochloride (7Ac)

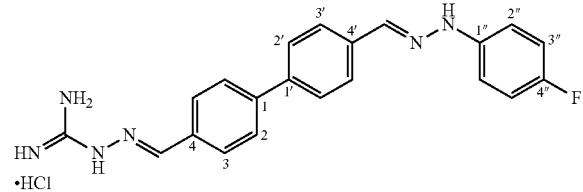 [SMILES: N=C(N)N/N=C/c1ccc(-c2ccc(/C=N/Nc3ccc(F)cc3)cc2)cc1 ; Cl]

Yield: 88%; mp >380° C. ¹H NMR (400 MHz, DMSO-d₆) δ 7.07 (d, J=7.6 Hz, 2H, H-2″), 7.09 (d, J=7.6 Hz, 2H, H-3″), 7.73 (s, 4H, H-2 and H-2′), 7.82 (br s, 4H, CH=NNHC(NH₂)=NH₂⁺), 7.84 (d, J=8.4 Hz, 2H, H-3′), 7.91 (s, 1H, CH=NNHAr), 7.98 (d, J=8.4 Hz, 2H, H-3), 8.24 (s, 1H, CH=NNHC(NH₂)=NH₂⁺), 10.5 (br s, 1H, CH=NNHAr), 12.08 (br s, 1H, CH=NNHC(NH₂)=NH₂⁺). ¹³C NMR (100 MHz, DMSO-d₆) δ 113 (C-2″), 115.6 (C-3″), 126.2 (C-2′), 126.6 (C-2), 127.0 (C-3′), 128.2 (C-3), 133.0 (C-1′), 135 (C-1), 136 (CH=NNHAr), 138.8 (C-4′), 140.9 (C-4), 141.9 (C-1″), 146.3 (CH=NNHC(NH₂)=NH₂⁺), 155.4 (CH=NNHC(NH₂)=NH₂⁺), 156.4 (C-4″). HRMS (nEI) Calcd. for C₂₁H₂₀FN₆ [M+H]⁺: 375.1728. Found: 375.1728. Anal. Calcd. for C₂₁H₂₀ClFN₆: C, 61.39; H, 4.94; N, 20.18. Found: C, 61.48; H, 4.94; N, 20.18.

(E)-2-((4′-((E)-(2-(4-Chlorophenyl)hydrazono) methyl)-[1,1′-biphenyl]-4-yl)methylene)hydrazine-1-carboximidamide monohydrochloride (7Ad)

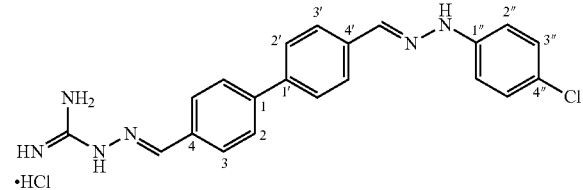 [SMILES: N=C(N)N/N=C/c1ccc(-c2ccc(/C=N/Nc3ccc(Cl)cc3)cc2)cc1 ; Cl]

Yield: 80%; mp >380° C. ¹H NMR (400 MHz, DMSO-d₆) δ 7.10 (d, J=8.4 Hz, 2H, H-2″), 7.26 (d, J=8.4 Hz, 2H, H-3″), 7.74 (br s, 4H, CH=NNHC(NH₂)=NH₂⁺), 7.74 (s, 4H, H-2 and H-2′), 7.84 (d, J=8.4 Hz, 2H, H-3′), 7.93 (s, 1H, CH=NNHAr), 7.98 (d, J=8.4 Hz, 2H, H-3), 8.23 (s, 1H, CH=NNHC(NH₂)=NH₂⁺), 10.65 (br s, 1H, CH=NNHAr), 12.05 (br s, 1H, CH=NNHC(NH₂)=NH₂⁺). ¹³C NMR (100 MHz, DMSO-d₆) δ 113.5 (C-2″), 122.0 (C-4″), 126.3 (C-2′), 126.7 (C-2), 127 (C-3′), 128.2 (C-3), 128.9 (C-3″), 133 (C-1′), 134.8 (C-1), 136.8 (CH=NNHAr), 139.0 (C-4′), 141.0 (C-4), 144.2 (C-1″), 146.4 (CH=NNHC(NH₂)=NH₂⁻), 155.4 (CH=NNHC(NH₂)=NH₂⁺). HRMS (nEI) Calcd. for C₂₁H₂₀ClN₆ [M+H]⁺: 391.1432. Found: 391.1431. Anal. Calcd. for C₂₁H₂₀Cl₂N₆: C, 59.02; H, 4.72; N, 19.67. Found: C, 59.22, H, 4.75; N, 19.46.

(E)-2-((4′-((E and Z)-(2-(4-Cyanophenyl)hydrazono) methyl)-[1,1′-biphenyl]-4-yl)methylene)hydrazine-1-carboximidamide monohydrochloride (7Ae)

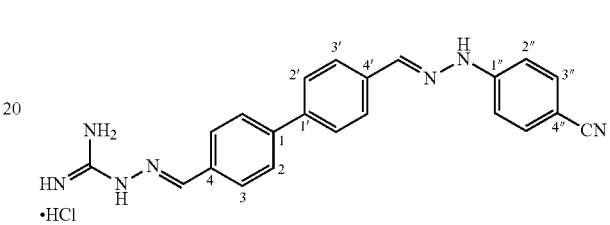

Yield: 33%; mp 308-310° C. ¹H NMR (400 MHz, DMSO-d₆) δ 7.19 (d, J=8.4 Hz, 2H, H-2″), 7.64 (d, J=8.4 Hz, 2H, H-3″), 7.4-7.8 (br s, 4H, CH=NNHC(NH₂)=NH₂⁺), 7.76-7.85 (m, 6H, H-2, H-2′, and H-3′); 7.973 and 7.981 (two d, J=8.0 Hz, 2H, 58:42 ratio of anti:syn H-3), 8.036 and 8.041 (two s, 1H, 58:42 ratio of anti:syn CH=NNHAr), 8.220 and 8.226 (two s, 1H, 58:42 ratio of anti:syn CH=NNHC(NH₂)=NH₂⁺), 11.12 and 11.16 (two br s, 1H, 58:42 ratio of anti:syn CH=NNHAr), 11.87 and 11.93 (two br s, 1H, 58:42 ratio of anti:syn CH=NNHC(NH₂)=NH₂⁺). ¹³C NMR (100 MHz, DMSO-d₆) δ 99.35 (syn Ar—CN), 99.40 (anti Ar—CN), 112.2 (C-2″), 120.1 (C-4″), 126.74 (anti C-2), 126.82 (syn C-2′), 126.819 (anti C-3′), 126.98 (syn C-3′), 132.69 (anti C-1′), 132.98 (syn C-1′), 133.7 (C-3″), 134.4 (syn C-1), 134.7 (anti C-1), 139.3 and 139.5 (syn:anti CH=NNHAr), 139.57 and 139.60 (anti:syn C-4′), 140.96 and 141.2 (syn:anti C-4), 146.4 and 146.5 (syn:anti CH=NNHC(NH₂)=NH₂⁺), 148.54 (anti C-1″), 148.55 (syn C-1″), 155.26 and 155.3 (anti:syn CH=NNHC(NH₂)=NH₂⁺). HRMS (nEI) Calcd. for C₂₂H₁₉ClN₇ [M+H]⁺: 382.1775. Found: 382.1771. Anal. Calcd. for C₂₂H₂₀ClN₇: C, 63.23; H, 4.82; N, 23.46. Found: C, 63.17; H, 4.80; N, 23.16.

(E)-2-((4′-((E)-(2-(2,4-Difluorophenyl)hydrazono) methyl)-[1,1′-biphenyl]-4-yl)methylene) hydrazine-1-carboximidamide, monohydrochloride (7Af)

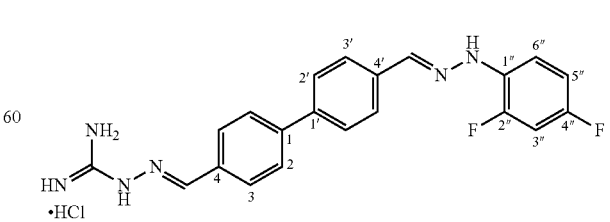

Yield: 84%; mp >380° C. ¹H NMR (400 MHz, DMSO-d₆) δ 7.02 (dt, J=9.6 and 2.8 Hz, 1H, (H-3″), 7.22 (ddd, J=11.6, 8.4, and 2.8 Hz, 1H, H-6"), 7.53 (dd, J=9.6 and 6.0 Hz, 1H, H-5"), 7.74 (br s, 4H, CH=NNHC(NH$_2$)=NH$_2^+$), 7.75 (s, 4H, H-2 and H-2'), 7.85 (d, J=8.4 Hz, 2H, H-3') 7.98 (d, J=8.4 Hz, 2H, H-3), 8.15 (s, 1H, CH=NNHC(NH$_2$)=NH$_2^+$), 8.22 (s, 1H, CH=NNHAr), 10.29 (br s, 1H, CH=NNHAr), 11.8 (br s, 1H, CH=NN HC(NH$_2$)=NH$_2^-$). $^{13}$C NMR (100 MHz, DMSO-d$_6$) δ 104.0 (C-6"), 111.5 (C-3"), 114.1 (C-5"), 126.5 (C-2'), 126.7 (C-2), 126.1 (C-3'), 128.3 (C-3), 130.3 (C-1"), 133.0 (C-1'), 134.8 (C-1), 139.0 (C-4'), 139.2 (C-4), 141.0 (CH=NNHAr), 146.3 (CH=NNHC(NH$_2$)=NH$_2^+$), 153.1 (C-4"), 155.6 (C-2"), 155.4 (CH=NNHC(NH$_2$)=NH$_2^+$). HRMS (nEI) Calcd. for C$_{21}$H$_{19}$N$_6$F$_2$ [M+H]$^+$: 393.1634. Found: 393.1631. Anal. Calcd. for C$_{21}$H$_{19}$N$_6$ClF$_2$: C, 58.81; H, 4.47; N, 19.60. Found: C, 58.37; H, 4.41; N, 19.44.

(E)-2-((4'-((E)-(2-(2,4-dichlorophenyl)hydrazono)methyl)-[1,1'-biphenyl]-4-yl)methylene)hydrazine-1-carboximidamide hydrochloride (7Ag)

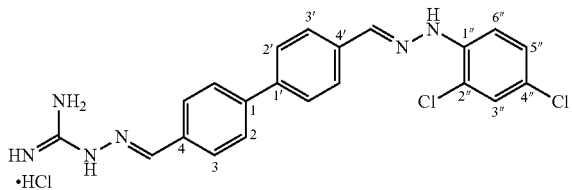 [SMILES: N=C(N)N/N=C/c1ccc(-c2ccc(/C=N/Nc3ccc(Cl)cc3Cl)cc2)cc1 ; Cl]

Yield: 80%; mp 356-358° C. $^1$H NMR (400 MHz, DMSO-d$_6$) δ 7.33 (d, J=8.8 and 2.4 Hz, 1H, H-5"), 7.48 (d, J=2.4 Hz, 1H, H-3"), 7.59 (d, J=8.8 Hz, 1H, H-6"), 7.5-8.2 (br s, 4H, C=HN—NH—C(NH$_2$)=NH$_2^+$), 7.77 (s, 4H, H-2', H-3', H-5', and H-6'), 7.84 (d, J=8.4 Hz, 2H, H-2 and H-6), 7.98 (d, J=8.4 Hz, 2H, H-3 and H-5), 8.22 (s, 1H, H—CH=N—NH—Ar), 8.35 (s, 1H, C H=N—NH—C(NH$_2$)=NH$_2^+$), 10.12 (s, 1H, CH=N—N H—Ar), 11.78 (s, 1H, CH=N—NH—C(NH$_2$)=NH$_2^+$). $^{13}$C NMR (100 MHz, DMSO-d$_6$) δ 116.7 C-6"), 122.3 (C-4"), 126.1 (C-2"), 126.75 (C-2), 126.85 (C-2'), 126.97 (C-3'), 128.1 (C-3), 128.6 (C-3"), 129.4 (C-5"), 133.0 (C-1'), 134.5 (C-1), 139.6 (C-4'), 140.5 (C-1"), 140.6 (CH=NNHAr), 140.7 (C-4), 146.5 (CH=NNHC(NH$_2$)=NH$_2^+$), 155.2 (CH=NNH C(NH$_2$)=NH$_2^+$). The observed CHN combustion analysis data (Found: C, 54.96; H, 4.04; N, 17.52 and C, 54.79; H, 4.19; N, 17.58) did not match pure 7Ag (Calcd: C, 56.40; H, 4.73; N, 17.16) but was consistent with 3.1% of (2E,2'E)-2,2'-([1,1'-biphenyl]-4,4'-diylbis(methanylylidene))-bis(hydrazine-1-carboximidamide) dihydrochloride$^1$ (3A).

(E)-2-(1-(4'-((E)-1-(2-(2-chlorophenyl)hydrazono)ethyl)-[1,1'-biphenyl]-4-yl)ethylidene)hydrazine-1-carboximidamide hydrochloride (8Aa)

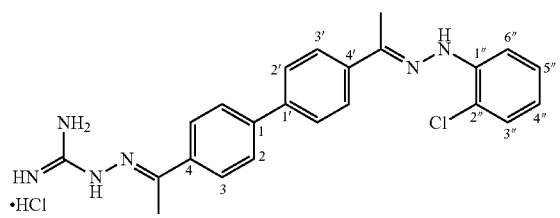 [SMILES: Cl ; C/C(=N\NC(=N)N)c1ccc(-c2ccc(/C(C)=N/Nc3ccccc3Cl)cc2)cc1]

Yield: 95%; mp >380° C. $^1$H NMR (400 MHz, DMSO-d$_6$) δ 2.36 (s, 3H, C(CH$_3$)=N—NH—Ar), 2.37 (s, 3H, C(C H$_3$)=N—NH—C(NH$_2$)=NH$_2^+$), 6.87 (dt, J=8.0 and 1.2 Hz, 1H, H-4"), 7.32 (dt, J=8.0 and 1.2 Hz, 1H, H-5"), 7.39 (dd, J=8.0 and 1.2 Hz, 1H, H-6"), 7.65 (dd, J=8.0 and 1.2 Hz, 1H, H-3"), 7.20-8.20 (br s, 4H, C(CH$_3$)=N—NH—C(N H$_2$)=NH$_2^+$), 7.78 (d, J=8.4 Hz, 2H, H-2' and H-6'), 7.79 (d, J=8.4 Hz, 2H, H-3' and 5'), 7.95 (d, J=8.4 Hz, 2H, H-2 and H-6), 8.08 (d, '=8.4 Hz, 2H, H-3 and H-5), 8.28 (s, 1H, C(CH$_3$)=N—NH—Ar), 10.83 (br s, 1H, C(CH$_3$)=N—N H—C(NH$_2$)=NH$_2^+$). $^{13}$C NMR (100 MHz, DMSO-d$_6$) δ 12.5 C(CH$_3$)=N—NH—Ar), 13.8 (C(CH$_3$)=N—NH—C(NH$_2$)=NH$_2^+$), 114.7 (C-2"), 117.5 (C-6"), 120.3 (C-4"), 126.2 (C-2'), 126.47 (C-3'), 126.5 (C-1), 127.4 (C-5"), 128.2 (C-3), 133.6 (C-1'), 137.7 (C-3"), 139.2 (C-4'), 140.3 (C-4), 141.4 (C-1"), 147.8 (C(CH$_3$)=N—NH—Ar), 151.4 (C(CH$_3$)=NNHC(NH$_2$)=NH$_2^+$), 155.7 (C(CH$_3$)=NNH C(NH$_2$)=NH$_2^+$). Anal. Calcd. for C$_{23}$H$_{24}$Cl$_2$N$_6$: C, 60.66; H, 5.31; N, 18.46. Found: C, 60.43; H, 5.28; N, 18.52.

Bacterial and Fungal Strains.

The bacterial strains *B. subtilis* 168 (strain A) was obtained from the *Bacillus* Genetic Stock Center (Ohio State University). *L. monocytogenes* ATCC 19115 (strain B), *A. baumannii* ATCC 19606 (strain E), *E. coli* MC1061 (strain G), *K. pneumoniae* ATCC 27736 (strain H), and *S. enterica* ATCC 14028 (strain J) were gifts from Dr. Paul Hergentorther (University of Illinois Champagne-Urbana). MRSA (strain C) and VRE (strain D) were obtained from Dr. David Sherman (University of Michigan). The *E. cloacae* ATCC 13047 (strain F) and *P. aeruginosa* ATCC 27853 (strain I) were gifts of Dr. Dev P. Arya (Clemson University). *M. smegmatis* MC2-155 (strain K) was obtained from Dr. Sabine Erht (Cornell University). The yeast strains *Candida albicans* ATCC 10231, *C. albicans* ATCC 64124, and *C. albicans* ATCC MYA-2876 were gifts from Dr. Jon Y. Takemoto (Utah State University, Logan, Utah, USA). The yeast strains *C. albicans* ATCC MYA-90819, *C. albicans* ATCC MYA-2310, *C. albicans* ATCC MYA-1237, and *C. albicans* ATCC MYA-1003 were obtained from the American Type Culture Collection (ATCC; Manassas, Va., USA).

Determination of MIC Values for Compounds 3A-B, 4A,C-H, 7Aa-Ag, and 8Aa as Antibacterials.

MIC values were determined against a variety of Gram-positive (strains A-D) and Gram-negative (E-J) bacterial and mycobacterial (K) strains using the double-dilution method, as previously published. Preliminary screening was performed using 500 μM of each compound. Compounds that were found to inhibit the growth of bacteria at 500 μM were then tested in a range of 0.5 to 250 μM, and bacteria were grown at 37° C. in Mueller-Hinton (MH) broth.

Development of Bacterial Resistance.

The development of resistance of *L. monocytogenes* ATCC 19115 (strain B), MRSA (strain C), VRE (strain D), and *P. aeruginosa* ATCC 27853 (strain I) to compounds 4D, 4F, and 7Aa as well as AMK as a reference was determined by following a previously published protocol. The bacteria were grown in MH broth at 37° C. for these experiments. Briefly, the ½ MIC concentration, from an active MIC experiments, was diluted 1:100 and grown overnight at 37° C. The resulting cultures were diluted 1:1000 and grown until the culture reached ~300,000 cfu/mL. That culture was then further diluted 1:1000 and used to determine the next round of MIC values. MIC values were determined every other day for a total of 15 rounds (Note: for the bacterial strains that developed resistance to compounds prior to the 15 passages, the MIC value determination was discontinued post resistance observation). The fold changes of the MIC values were determined and these data are presented in FIG. 2.

Determination of MIC Values for Compounds 3A-B, 4A,C-H, 7Aa-Ag, and 8Aa as Antifungals.

In vitro MIC testing was performed according to the CLSI M27-A3 standard microbroth dilution methodology for the susceptibility testing of yeasts with minor modifications. Briefly, serial dilutions of the test compounds as well as a reference compound, AmB, were prepared in RPMI 1640 medium (catalog # R6504, Sigma-Aldrich Chemical Co., St. Louis, Mo.) buffered to pH 7 with 0.165 M morpholinepropanesulfonic acid (MOPS) buffer (Sigma-Aldrich Chemical Co.) using 96-well plates in a range of 0.48-31.2 µg/mL, and microtiter plates were then incubated at 35° C. for 2 days. MIC values were read visually for all tested compounds, and the endpoint was determined as the minimum concentration of compound that yielded complete inhibition relative to growth control.

Development of Fungal Resistance.

C. albicans ATCC 10231 was used to perform the development of resistance of this strain to compounds 4F and 7Aa, as well as AmB as a reference. Firstly, MIC values of 4F, 7Aa, and POS against this strain were determined in 96-well plates using RPMI 1640 medium at 35° C. for 48 h. Aliquot of 10 µL from the well that was showing the ½ MIC values were subcultured into PDA and grown overnight at 35° C. A single colony was picked to inoculate fresh RPMI 1640 medium and that culture was used to determine the next round of MIC values. The MIC values for each compound were determined every third day for a total of 15 passages of MIC determination. The fold changes of the MIC values were determined and these data are presented in FIG. 2.

Assays for Reactive Oxygen Species (ROS) Production.

We used the 2',7'-dichlorodihydrofluorescein diacetate (DCFH-DA) dye as a probe to measure the production of ROS in yeast cells upon treatment with our compounds. DCFH-DA can easily cross the cell membranes and be hydrolyzed by cellular esterases to the non-fluorescent 2',7'-dichlorodihydrofluorescein (DCFH), which can further be oxidized to the highly fluorescent 2',7'-dichlorofluorescein (DCF) by the intracellular ROS. Five mL of RPMI 1640 medium were inoculated with a single colony of C. albicans ATCC 10231 (strain A) in a Falcon tube and grown overnight at 35° C. at 200 rpm. The overnight culture was diluted by adding 200 µL of yeast cells to 800 µL of the same medium. Cell suspension (100 µL) was added to the RPMI 1640 medium containing no drug (negative control) or compounds 4F and 7Aa at their 1× and 2× MIC values, and treated for 1 h at 35° C. $H_2O_2$ at 1 mM was also used as a positive control. Cells were centrifuged and washed twice with PBS buffer (pH 7.2). Cells were resuspended in the same buffer and incubated with DCFH-DA (20 µg/mL) for 30 min in the dark. Afterwards, cells were centrifuged and washed with PBS buffer to remove excess DCFH-DA. Glass slides with 10-15 µL of each mixture were prepared and observed in bright field and fluorescence modes (FITC filter set, excitation and emission wavelengths of 488 and 512 nm, respectively) using a Zeiss Axovert 200M fluorescence microscope (FIG. 3).

Toxicity Studies.

Cytotoxicity assays were performed as previously described. The human lung carcinoma epithelial cells A549 and the normal human bronchial epithelial cells BEAS-2B were grown in F12-K and DMEM medium containing 10% fetal bovine serum (FBS) and 1% antibiotics, respectively. The confluent cells were trypsinized with 0.05%-trypsin-0.53 mM EDTA, centrifuged (1,200 rpm) and resuspended in fresh medium (F12-K or DMEM). The cells were seeded into 96-well microtiter plates at a density of 3,000 cells/well and were grown overnight. The following day, the media were replaced by 100 µL of fresh culture media containing serially diluted compounds 3A-B, 4A,C-H, and 7Aa-Af, as well as a reference compound, AmB, (at final concentrations of 0.24-31.2 µg/mL or sterile dd$H_2O$ (negative control). The cells were incubated for an additional 24 h at 37° C. with 5% $CO_2$ in a humidified incubator. Each well was treated with 10 µL (25 µg/mL) of resazurin sodium salt (Sigma-Aldrich) for 3-6 h to determine cell viability. Metabolically active cells can convert the blue non-fluorescent dye resazurin to the pink and highly fluorescent dye resorufin, which can be detected at $A_{560}$ excitation and $A_{590}$ emission wavelengths by using a SpectraMax M5 plate reader. Triton X-100® (0.5%, v/v) gave complete loss of cell viability and was used as the positive control. The percent cell survival was calculated as: (test value/control value)×100, where control value represents cells+resazurin–drug, and test value represents cells+resazurin+drug. These data are presented in FIGS. 4A-B.

Cell-Based [$^3$H]Dofetilide Binding Assay.

HEK-293 cell membranes which specifically and stably express the hERG channel protein were prepared and harvested as previously described. Assays were conducted in duplicate, and three independent assays were performed for each compound that was evaluated. Cell membrane suspension (5 µg) was added to duplicate tubes containing assay buffer (50 mM Tris, 10 mM KCl, and 1 mM $MgCl_2$, pH 7.4), 25 µL of a single concentration of analogue (a concentration range of 10 nM-100 µM was employed for each experiment), and 25 µL of [$^3$H]dofetilide (5 nM, final concentration) for an assay volume of 250 µL. Nonspecific binding was assessed in the presence of 1 mM amitriptyline. Binding occurred for 60 min at 25° C. and was terminated by rapid filtration through Whatman GF/B filters, which were pre-soaked in 0.5% PEI for 2 h. Filters were washed three times with ~1 mL of ice-cold assay buffer. Radioactivity retained by the filters was determined by liquid scintillation counting by using a Tri-Carb 2100TR liquid scintillation analyzer (PerkinElmer Life and Analytical Sciences, Boston, Mass.). These data are presented in FIG. 5.

In summary, amidinohydrazone compounds such as nine bis(N-amidino)hydrazones and eight N-amidino-N'-aryl-bishydrazones were shown to have antifungal activity and their activity was not readily predicable from their antibacterial activity. In addition, the amidinohydrazone compounds displayed low potential for resistance development, and were found to induce ROS production in a C. albicans strain. They were also found to display reasonable toxicity profiles against two mammalian cell lines as well as only moderate, acceptable hERG channel inhibition. In light of our SAR study, compounds 4F, 7Ac, and 7Af, were preferred embodiments of the disclosure.

Only the preferred embodiment of the present invention and examples of its versatility are shown and described in the present disclosure. It is to be understood that the present invention is capable of use in various other combinations and environments and is capable of changes or modifications within the scope of the inventive concept as expressed herein. Thus, for example, those skilled in the art will recognize, or be able to ascertain, using no more than routine experimentation, numerous equivalents to the specific substances, procedures and arrangements described herein.

Such equivalents are considered to be within the scope of this invention, and are covered by the following claims.

REFERENCES

1. Prevention, C. f. D. C. a. Office of Infectious Disease Antibiotic Resistance Threats in the United States. In 2013.
2. Dantes, R.; Mu, Y.; Belflower, R.; Aragon, D.; Dumyati, G.; Harrison, L. H.; Lessa, F. C.; Lynfield, R.; Nadle, J.; Petit, S.; Ray, S. M.; Schaffner, W.; Townes, J.; Fridkin, S.; Emerging Infections Program-Active Bacterial Core Surveillance, M. S. I. National burden of invasive methicillin-resistant *Staphylococcus aureus* infections, United States, 2011. *JAMA Intern Med* 2013, 173, 1970-8.
3. Scallan, E.; Hoekstra, R. M.; Angulo, F. J.; Tauxe, R. V.; Widdowson, M. A.; Roy, S. L.; Jones, J. L.; Griffin, P. M. Foodborne illness acquired in the United States—major pathogens. *Emerg Infect Dis* 2011, 17, 7-15.
4. Fridkin, S. K.; Jarvis, W. R. Epidemiology of nosocomial fungal infections. *Clin Microbiol Rev* 1996, 9, 499-511.
5. Sievert, D. M.; Ricks, P.; Edwards, J. R.; Schneider, A.; Patel, J.; Srinivasan, A.; Kallen, A.; Limbago, B.; Fridkin, S.; National Healthcare Safety Network, T.; Participating, N. F. Antimicrobial-resistant pathogens associated with healthcare-associated infections: summary of data reported to the National Healthcare Safety Network at the Centers for Disease Control and Prevention, 2009-2010. *Infect Control Hosp Epidemiol* 2013, 34, 1-14.
6. Wisplinghoff, H.; Bischoff, T.; Tallent, S. M.; Seifert, H.; Wenzel, R. P.; Edmond, M. B. Nosocomial bloodstream infections in US hospitals: analysis of 24,179 cases from a prospective nationwide surveillance study. *Clin Infect Dis* 2004, 39, 309-17.
7. Nguewa, P. A.; Fuertes, M. A.; Cepeda, V.; Iborra, S.; Carrion, J.; Valladares, B.; Alonso, C.; Perez, J. M. Pentamidine is an antiparasitic and apoptotic drug that selectively modifies ubiquitin. *Chem Biodivers* 2005, 2, 1387-400.
8. Bilik, P.; Tanious, F.; Kumar, A.; Wilson, W. D.; Boykin, D. W.; Colson, P.; Houssier, C.; Facompre, M.; Tardy, C.; Bailly, C. Novel dications with unfused aromatic systems: trithiophene and trifuran derivatives of furimidazoline. *Chembiochem* 2001, 2, 559-69.
9. Rollas, S.; Kucukguzel, S. G. Biological activities of hydrazone derivatives. *Molecules* 2007, 12, 1910-39.
10. Bedia, K. K.; Elcin, O.; Seda, U.; Fatma, K.; Nathaly, S.; Sevim, R.; Dimoglo, A. Synthesis and characterization of novel hydrazide-hydrazones and the study of their structure-antituberculosis activity. *Eur J Med Chem* 2006, 41, 1253-61.
11. Kucukguzel, G.; Kocatepe, A.; De Clercq, E.; Sahin, F.; Gulluce, M. Synthesis and biological activity of 4-thiazolidinones, thiosemicarbazides derived from diflunisal hydrazide. *Eur J Med Chem* 2006, 41, 353-9.
12. Chang, L.; Whittaker, N. F.; Bewley, C. A. Crambescidin 826 and dehydrocrambine A: new polycyclic guanidine alkaloids from the marine sponge *Monanchora* sp. that inhibit HIV-1 fusion. *J Nat Prod* 2003, 66, 1490-4.
13. Kucukguzel, S. G.; Mazi, A.; Sahin, F.; Ozturk, S.; Stables, J. Synthesis and biological activities of diflunisal hydrazide-hydrazones. *Eur J Med Chem* 2003, 38, 1005-13.
14. Sidoryk, K.; Switalska, M.; Jaromin, A.; Cmoch, P.; Bujak, I.; Kaczmarska, M.; Wietrzyk, J.; Dominguez, E. G.; Zarnowski, R.; Andes, D. R.; Bankowski, K.; Cybulski, M.; Kaczmarek, L. The synthesis of indolo[2,3-b] quinoline derivatives with a guanidine group: highly selective cytotoxic agents. *Eur J Med Chem* 2015, 105, 208-19.
15. Todeschini, A. R.; de Miranda, A. L. P.; da Silva, K. C. M.; Parrini, S. C.; Barreiro, E. J. Synthesis and evaluation of analgesic, antiinflammatory and antiplatelet properties of new 2-pyridylarylhydrazone derivatives. *Eur J Med Chem* 1998, 33, 189-199.
16. Said, M.; Badshah, A.; Shah, N. A.; Khan, H.; Murtaza, G.; Vabre, B.; Zargarian, D.; Khan, M. R. Antitumor, antioxidant and antimicrobial studies of substituted pyridylguanidines. *Molecules* 2013, 18, 10378-96.
17. Melnyk, P.; Leroux, V.; Sergheraert, C.; Grellier, P. Design, synthesis and in vitro antimalarial activity of an acylhydrazone library. *Bioorg Med Chem Lett* 2006, 16, 31-5.
18. Laville, R.; Thomas, O. P.; Bernie, F.; Marquez, D.; Vacelet, J.; Amade, P. Bioactive guanidine alkaloids from two Caribbean marine sponges. *J Nat Prod* 2009, 72, 1589-94.
19. Fair, R. J.; Hensler, M. E.; Thienphrapa, W.; Dam, Q. N.; Nizet, V.; Tor, Y. Selectively guanidinylated aminoglycosides as antibiotics. *ChemMedChem* 2012, 7, 1237-44.
20. Gursoy, A.; Terzioglu, N.; OtUk, G. Synthesis of some new hydrazide-hydrazones, thiosemicarbazides and thiazolidinones as possible antimicrobials. *Eur J Med Chem* 1997, 32, 653-757.
21. Hua, H.-M.; Peng, J.; Dunbar, D. C.; Schinazi, R. F.; de Castro Andrews, A. G.; Cuevas, C.; Garcia-Fernandez, L. F.; Kelly, M.; Hamann, M. T. Batzelladine alkaloids from the caribbean sponge *Monanchora unguifera* and the significant activities against HIV-1 and AIDS opportunistic infectious pathogens. *Tetrahedron* 2007, 63, 11179-11188.
22. Ozdemir, A.; Turan-Zitouni, G.; Kaplancikli, Z. A.; Demirci, F.; Iscan, G. Studies on hydrazone derivatives as antifungal agents. *J Enz Inhib Med Chem* 2008, 23, 470-475.
23. Kibirev, V. K.; Osadchuk, T. V.; Kozachenko, O. P.; Kholodovych, V.; Fedoryak, D.; Brovarets, V. S. Synthesis, biological evaluation and docking of novel bisamidinohydrazones as non-peptide inhibitors of furin. *Ukr Biochem J* 2015, 87, 55-63.
24. Calas, M.; Ouattara, M.; Piquet, G.; Ziora, Z.; Bordat, Y.; Ancelin, M. L.; Escale, R.; Vial, H. Potent antimalarial activity of 2-aminopyridinium salts, amidines, and guanidines. *J Med Chem* 2007, 50, 6307-15.
25. Boykin, D. W.; Kumar, A.; Spychala, J.; Zhou, M.; Lombardy, R. J.; Wilson, W. D.; Dykstra, C. C.; Jones, S. K.; Hall, J. E.; Tidwell, R. R.; et al. Dicationic diarylfurans as anti-*Pneumocystis carinii* agents. *J Med Chem* 1995, 38, 912-6.
26. Gambari, R.; Nastruzzi, C. DNA-binding activity and biological effects of aromatic polyamidines. *Biochem Pharmacol* 1994, 47, 599-610.
27. Bielawski, K.; Bielawska, A.; Wolczynski, S. Aromatic extended bisamidines: synthesis, inhibition of topoisomerases, and anticancer cytotoxicity in vitro. *Arch Pharm (Weinheim)* 2001, 334, 235-40.
28. Nakayama, T.; Taira, S.; Ikeda, M.; Ashizawa, H.; Oda, M.; Arakawa, K.; Fujii, S. Synthesis and structure-activity study of protease inhibitors. V. Chemical modification of 6-amidino-2-naphthyl 4-guanidinobenzoate. *Chem Pharm Bull* (Tokyo) 1993, 41, 117-25.

29. Cavallini, G.; Massarani, E.; Nardi, D.; Mauri, L.; Mantegazza, P. Antibacterial agents. Some new guanylhydrazone derivatives. *J Med Pharm Chem* 1961, 4, 177-82.
30. Belenky, P.; Camacho, D.; Collins, J. J. Fungicidal drugs induce a common oxidative-damage cellular death pathway. *Cell Rep* 2013, 3, 350-8.
31. Delattin, N.; Cammue, B. P.; Thevissen, K. Reactive oxygen species-inducing antifungal agents and their activity against fungal biofilms. *Future Med Chem* 2014, 6, 77-90.
32. Ngo, H. X.; Shrestha, S. K.; Garneau-Tsodikova, S. Identification of ebsulfur analogues with broad spectrum antifungal activity. *ChemMedChem* 2016.
33. Li, Y.; Chang, W.; Zhang, M.; Li, X.; Jiao, Y.; Lou, H. Diorcinol D Exerts Fungicidal Action against *Candida albicans* through Cytoplasm Membrane Destruction and ROS Accumulation. *PLoS One* 2015, 10, e0128693.
34. Curran, M. E.; Splawski, I.; Timothy, K. W.; Vincent, G. M.; Green, E. D.; Keating, M. T. A molecular basis for cardiac arrhythmia: HERG mutations cause long QT syndrome. *Cell* 1995, 80, 795-803.
35. Fermini, B.; Fossa, A. A. The impact of drug-induced QT interval prolongation on drug discovery and development. *Nat Rev Drug Discov* 2003, 2, 439-47.

What is claimed is:

1. A method for treating a fungal infection, the method comprising administering to a subject in need thereof a therapeutically effective amount of a compound according to formula (I):

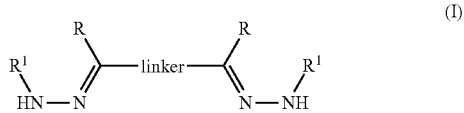

(I)

or a pharmaceutically acceptable salt thereof, wherein each R is independently H or a lower alkyl, wherein each $R^1$ is independently an amidino or a phenyl, and wherein the linker is

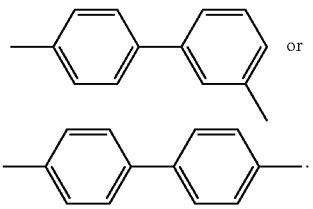

2. The method of claim 1, wherein the compound is according to formula (III):

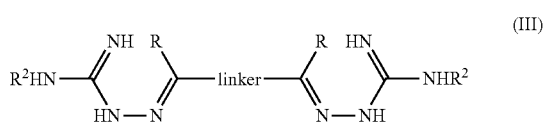

(III)

or a pharmaceutically acceptable salt thereof; wherein each R2 is independently selected from the group consisting of H, a lower alkyl, a phenyl, a substituted lower alkyl, or a substituted phenyl.

3. The method of claim 1, wherein the compound is according to formula (IV):

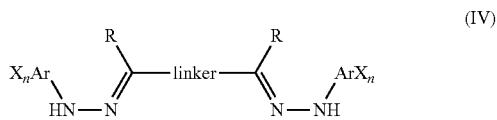

(IV)

or a pharmaceutically acceptable salt thereof; wherein Ar is a phenyl group; wherein each X is independently selected from the group consisting of an electron-withdrawing group selected from the group consisting of a halogen, a carbonyl group, sulfoxide, sulfone, sulfonate, sulfonamide, a nitro group, a cyano group; and wherein each n is independently between 0 and 5, with 0 representing an unsubstituted phenyl group.

4. The method of claim 3, wherein each X is independently selected from the group consisting of fluorine, chlorine, and bromine.

5. The method of claim 1, wherein the compound is according to formula (V):

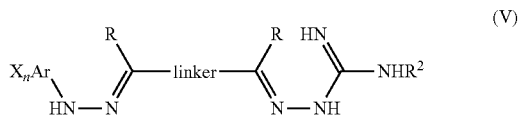

(V)

or a pharmaceutically acceptable salt thereof; wherein Ar is a phenyl group; wherein each X is independently selected from the group consisting of an electron-withdrawing group selected from the group consisting of a halogen, a carbonyl group, sulfoxide, sulfone, sulfonate, sulfonamide, a nitro group, a cyano group; wherein n is between 0 and 5, with 0 representing an unsubstituted phenyl group; and wherein R2 is selected from the group consisting of H, a lower alkyl, a phenyl, a substituted lower alkyl, or a substituted phenyl.

6. The method of claim 5, wherein each X is independently selected from the group consisting of fluorine, chlorine, and bromine.

7. The method of claim 1, wherein the compound is a pharmaceutically acceptable hydrochloride salt.

8. The method of claim 1, wherein the compound is selected from the group consisting of:

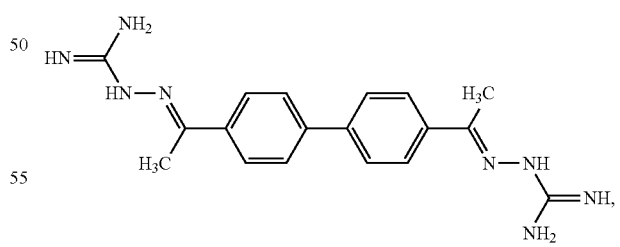

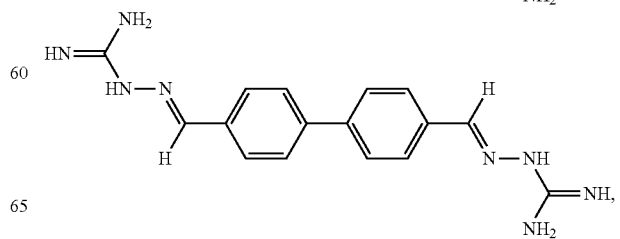

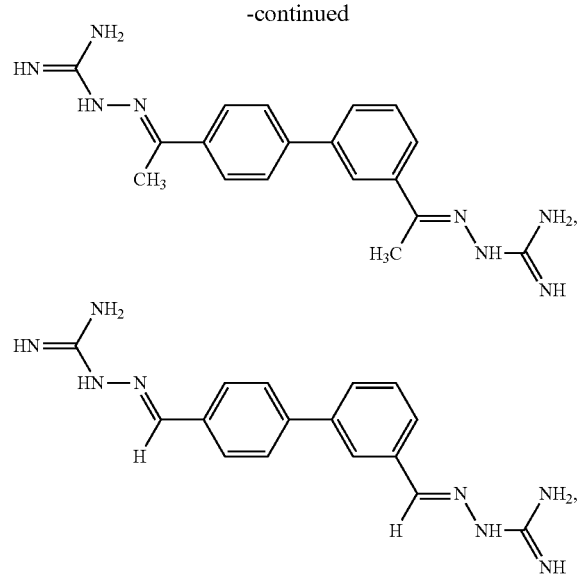
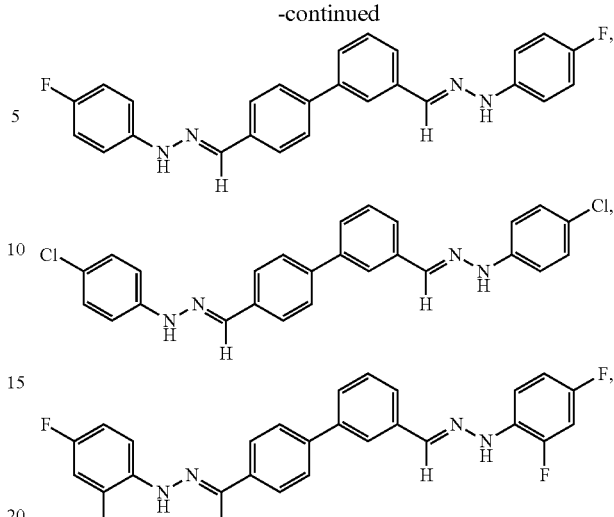
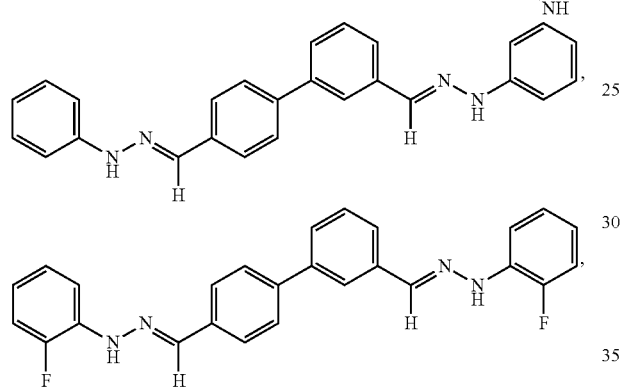
and
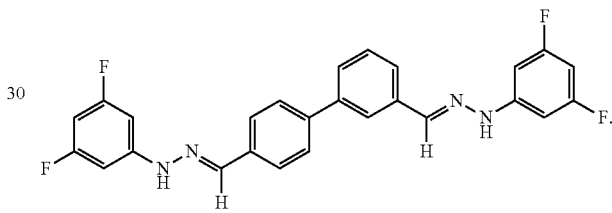
* * * * *